United States Patent
Rochkind et al.

(10) Patent No.: US 10,729,815 B2
(45) Date of Patent: Aug. 4, 2020

(54) COMBINED TREATMENT FOR NERVE INJURIES

(71) Applicants: Ramot at Tel-Aviv University Ltd., Tel-Aviv (IL); The Medical Research, Infrastructure and Health Services Fund of the Tel Aviv Medical Center, Tel Aviv (IL)

(72) Inventors: Shimon Rochkind, Tel-Aviv (IL); Zvi Nevo, Herzlia (IL)

(73) Assignees: Ramot at Tel-Aviv University Ltd., Tel-Aviv (IL); The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 16/302,694

(22) PCT Filed: Nov. 29, 2017

(86) PCT No.: PCT/IB2017/057501
§ 371 (c)(1),
(2) Date: Nov. 19, 2018

(87) PCT Pub. No.: WO2018/100511
PCT Pub. Date: Jun. 7, 2018

(65) Prior Publication Data
US 2019/0117846 A1     Apr. 25, 2019

Related U.S. Application Data

(60) Provisional application No. 62/428,621, filed on Dec. 1, 2016.

(51) Int. Cl.

| | | |
|---|---|---|
| *A61L 27/52* | (2006.01) | |
| *A61L 27/26* | (2006.01) | |
| *A61L 27/58* | (2006.01) | |
| *A61L 27/22* | (2006.01) | |
| *A61L 27/24* | (2006.01) | |
| *A61L 27/36* | (2006.01) | |
| *C12N 9/02* | (2006.01) | |
| *C12N 9/16* | (2006.01) | |

(52) U.S. Cl.
CPC .......... *A61L 27/52* (2013.01); *A61L 27/227* (2013.01); *A61L 27/24* (2013.01); *A61L 27/26* (2013.01); *A61L 27/3675* (2013.01); *A61L 27/58* (2013.01); *C12N 9/0089* (2013.01); *C12N 9/16* (2013.01); *A61L 2300/25* (2013.01); *A61L 2300/254* (2013.01); *A61L 2430/32* (2013.01); *C12Y 115/01001* (2013.01); *C12Y 301/06004* (2013.01)

(58) Field of Classification Search
CPC combination set(s) only.
See application file for complete search history.

(56) References Cited

U.S. PATENT DOCUMENTS 7,772,185 B2 * 8/2010 English ................. A61K 38/47
514/17.7
2014/0187487 A1 7/2014 Shoichet et al.

FOREIGN PATENT DOCUMENTS

| WO | WO 2009/022339 | 2/2009 |
| WO | WO 2018/100511 | 6/2018 |
| WO | WO 2019/106671 | 6/2019 |

OTHER PUBLICATIONS

International Search Report and the Written Opinion dated Mar. 20, 2018 From the International Searching Authority Re. Application No. PCT/IB2017/057501. (18 Pages).
Barritt et al. "Chondroitinase ABC Promotes Sprouting of Intact and Injured Spinal Systems After Spinal Cord Injury", Journal of Neuroscience, 26(42): 10856-10867, Oct. 18, 2006.
Bradbury et al. "Chondroitinase ABC Promotes Functional Recovery After Spinal Cord Injury", Nature, 416(6881): 636-640, Apr. 11, 2002.
Buchli et al. "Inhibition of Nogo: A Key Strategy to Increase Regeneration, Plasticity and Functional Recovery of the Lesioned Central Nervous System", Annals of Medicine, XP055456135, 37(8): 556-567, Jan. 2005.
Hou et al. "The Enhancement of Cell Adherence and Inducement of Neurite Outgrowth of Dorsal Root Ganglia Co-Cultured With Hyaluronic Acid Hydrogels Modified With Nogo-66 Receptor Antagonist In Vitro", Neuroscience, XP024986465, 137(2): 519-529, Jan. 2006. Abstract, p. 519, r-h Col., Para 2-p. 520, 1-h Col., Para 2, p. 528, 1-h Col., Para 3.
Itoh et al. "Effects of A Laminin Peptide (YIGSR) Immobilized on Crab-Tendon Chitosan Tubes on Nerve Regeneration", Journal of Biomedical Materials Research Part B: Applied Biomaterials, 73(2): 375-382, Published Online Mar. 7, 2005.
Kabu et al. "Drug Delivery, Cell-Based Therapies, and Tissue Engineering Approaches for Spinal Cord Injury", Journal of Controlled Release, XP029303662, 219: 141-154, Available Online Sep. 4, 2015. Chaps.1.4.1, 1.4.2, 1.4.6.1, 1.4.8.
Rossi et al. "Sustained Delivery of Chondroitinase ABC From Hydrogel System", Journal of Functional Biomaterials, XP055456184, 3(4): 199-208, Mar. 19, 2012. Abstract, p. 200, Para 3, p. 206, Para 3, 4.
Suzuki et al. "Tendon Chitosan Tubes Covalently Coupled With Synthesized Laminin Petptides Facilitate Nerve Regeneration In Vivo", Journal of Neuroscience Research, 72(5): 646-659, Jun. 1, 2003.

(Continued)

*Primary Examiner* — Kimberly Ballard
*Assistant Examiner* — Stacey N MacFarlane

(57) ABSTRACT

A combined treatment for nerve injury is provided. Accordingly there is provided a composition comprising a hyaluronic acid, a laminin polypeptide, an antioxidant and an anti-gliotic agent. Also provided are matrices and hydrogels of the composition and methods of using same.

19 Claims, 3 Drawing Sheets
(2 of 3 Drawing Sheet(s) Filed in Color)
Specification includes a Sequence Listing.

(56) References Cited

OTHER PUBLICATIONS

Barritt et al. "Chondroitinase ABC Promotes Sprouting of Intact and Injured Spinal Systems After Spinal Cord Injury", The Journal of Neuroscience, 26(4): 10856-10867, Oct. 18, 2006.

Coviello et al. "Polysaccharide Hydrogels for Modified Release Formulations", Journal of Controlled Release, 119(1): 5-24, Available Online Jan. 19, 2007.

Hallmann et al. "Expression and Function of Laminins in the Embryonic and Mature Vasculature", Physiological Reviews, 85(3): 979-1000, Jul. 2005.

Ho et al. "Preparation and Characterization of RGD-Immobilized Chitosan Scaffolds", Biomaterials, 26(6): 3197-3206, Available Online Oct. 14, 2004.

Hou et al. "The Repair of Brain Lesion by Implantation of Hyaluronic Acid Hydrogels Modified With Laminin", Journal of Neuroscience Methods, 148(1): 60-70, Published Online Jun. 22, 2005.

Itoh et al. "Effects of A Laminin Peptide (YIGSR) Immobilized on Crab-Tendon Chitosan Tubes on Nerve Regeneration", Journal of Biomedical Material Research, Part B: Applied Biomaterils, 73B(2): 375-382, Published Online Mar. 7, 2005.

Lee et al. "Nogo Receptor Antagonism Promotes Stroke Recovery by Enhancing Axonal Plasticity", The Journal of Neuroscience, 24(27): 6209-6217, Jul. 7, 2004.

Li et al. "Blockade of Nogo-66, Myelin-Associated Glycoprotein, and OligodendrocyteMyelin Glycoprotein by Soluble Nogo-66 Receptor Promotes Axonal Sproutin and Recovery After Spinal Injury", The Journal of Neuroscience, 24(46): 10511-10520, Nov. 17, 2004.

Liu et al. "Extracellular Regulators of Axonal Growth inthe Adult Central Nervous System", Philosophical Transactions of the Royal Society B, 361(1473): 1593-1610, Published Online Jul. 31, 2006.

Matsuda et al. "Immobilization of Laminin Peptide in Molecularly Aligned Chitosan by Covalent Bonding", Biomaterials, 26(15): 2273-2279, Available Online Sep. 16, 2004.

Moore et al. "Restoration of Axon Conduction and Motor Deficits by Therapeutic Treatment With Glatiramer Acetate", Journal of Neuroscience Research, 92(12): 1621-1636, Published Online Jul. 2, 2014.

Niece et al. "Self-Assembly Combining Two Bioactive Peptide-Amphiphile Molecules Into Nanofibers by Electrostatic Attraction", Journal of the American Chemical Society, 125(24): 7146-7147, Jun. 18, 2003.

Powell et al. "Neuronal Laminins and Their Cellular Receptors", The International Jounal of Biochemistry & Cell Biology, 29(3): 401-414, Mar. 1997.

Rossignol et al. "Spinal Cord Injury: Time to Move?", The Journal of Neuroscience, 27(44): 11782-11792, Oct. 31, 2007.

Scorisa et al. "Glatiramer Acetate Treatment Increses Stability of Spinal Synapses and Down Regulates MHC I During the Course of EAE", International Journal of Biological Sciences, 7(8): 1188-1202, Oct. 27, 2011.

Suzuki et al. "Tendon Chitosan Tubes Covalently Coupled With Synthesized Laminin Peptides Facilitate Nerve Regeneration In Vivo", Journal of Neuroscience Research, 72(5): 646-659, Jun. 2003.

Tashiro et al. "A Synthetic Peptide Containing the IKVAV Sequence From the A Chain of Laminin Mediates Cell Attachment, Migration, and Neurite Outgrowth", The Journal of Biological Chemistry, 264(27): 16174-16182, Sep. 25, 1989.

International Search Report and the Written Opinion dated Mar. 6, 2019 From the International Searching Authority Re. Application No. PCT/IL2018/051308. (16 Pages).

Rochkind et al. "Recovery of Peripheral Nerve with Massive Loss Defect by Tissue Engineered Guiding Regenerative Gel", BioMed Research International, XP055558667, 2014(Article ID 327578):1-7,, Jan. 1, 2014.

\* cited by examiner

Control – no treatment

No movement

GRG implantation

Slight Active movement

AGRG implantation

Active movement

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: synthetic amino acids sequence simulating
      laminin

<400> SEQUENCE: 1

Lys Ser Ile Lys Val Ala Val Arg Ser Tyr Ile Gly Ser Arg Cys Val
1               5                   10                  15

<210> SEQ ID NO 2
<211> LENGTH: 5
<212> TYPE: PRT
<213> ORGANISM: Artificial Sequence
<220> FEATURE:
<223> OTHER INFORMATION: penta-peptide epitope of laminin responsible
      for promoting neuronal outgrowth

<400> SEQUENCE: 2

Ile Lys Val Ala Val
1               5

<210> SEQ ID NO 3
<211> LENGTH: 5
<212> TYPE: PRT
<213> ORGANISM: Artificial Sequence
<220> FEATURE:
<223> OTHER INFORMATION: penta-peptide epitope  of laminin responsible
      for promoting cell substrate adhesion

<400> SEQUENCE: 3

Tyr Ile Gly Ser Arg
1               5

<210> SEQ ID NO 4
<211> LENGTH: 154
<212> TYPE: PRT
<213> ORGANISM: Homo sapiens
```

<400> SEQUENCE: 4

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 5
<211> LENGTH: 981
<212> TYPE: DNA
<213> ORGANISM: Homo sapiens

<400> SEQUENCE: 5

```
gtttggggcc agagtgggcg aggcgcggag gtctggccta taaagtagtc gcggagacgg    60
ggtgctggtt tgcgtcgtag tctcctgcag cgtctggggt ttccgttgca gtcctcggaa   120
ccaggacctc ggcgtggcct agcgagttat ggcgacgaag gccgtgtgcg tgctgaaggg   180
cgacggccca gtgcagggca tcatcaattt cgagcagaag gaaagtaatg gaccagtgaa   240
ggtgtgggga agcattaaag gactgactga aggcctgcat ggattccatg ttcatgagtt   300
tggagataat acagcaggct gtaccagtgc aggtcctcac tttaatcctc tatccagaaa   360
acacggtggg ccaaaggatg aagagaggca tgttggagac ttgggcaatg tgactgctga   420
caaagatggt gtggccgatg tgtctattga agattctgtg atctcactct caggagacca   480
ttgcatcatt ggccgcacac tggtggtcca tgaaaaagca gatgacttgg gcaaggtgg    540
aaatgaagaa agtacaaaga caggaaacgc tggaagtcgt ttggcttgtg gtgtaattgg   600
gatcgcccaa taaacattcc cttggatgta gtctgaggcc ccttaactca tctgttatcc   660
tgctagctgt agaaatgtat cctgataaac attaaacact gtaatcttaa agtgtaatt    720
gtgtgacttt ttcagagttg ctttaaagta cctgtagtga gaaactgatt tatgatcact   780
tggaagattt gtatagtttt ataaaactca gttaaaatgt ctgtttcaat gacctgtatt   840
ttgccagact taaatcacag atgggtatta aacttgtcag aatttctttg tcattcaagc   900
ctgtgaataa aaaccctgta tggcacttat tatgaggcta ttaaagaat ccaaattcaa    960
actaaaaaaa aaaaaaaaa a                                              981
```

COMBINED TREATMENT FOR NERVE INJURIES

RELATED APPLICATIONS

This application is a National Phase of PCT Patent Application No. PCT/IB2017/057501 having International filing date of Nov. 29, 2017, which claims the benefit of priority under 35 USC § 119(e) of U.S. Provisional Patent Application No. 62/428,621 filed on Dec. 1, 2016. The contents of the above applications are all incorporated by reference as if fully set forth herein in their entirety.

SEQUENCE LISTING STATEMENT

The ASCII file, entitled 73639SequenceListing.txt, created on Nov. 19, 2018, comprising 3,915 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to combined treatment for nerve injury.

Central nervous system (CNS) injuries such as spinal cord injury (SCI) have no successful treatment to date. SCI is associated with an immediate loss of sensory and motor locomotion with permanent deficit in reflex functions below the level of injury. Furthermore, CNS injuries are usually characterized by total failure to regenerate and heal. Immediate events which occur following SCI include ischemia, an immune response activating microglia cells and infiltration of injured cells from the neighboring vascular tissues, due to apoptotic and necrotic damages to capillary blood vessels. The injury is simultaneously accompanied by nonspecific reactive changes of glial cells e.g. astrocytes and macrophages in response to the damage including secretion of connective tissue matrix substances such as proteoglycans (PGs), collagens and myelin-derived residues. These substances lead to formation of a scar tissue resulting in inhibition of axons sprouting and restricting neuronal regeneration. Indeed, scientific reports describe treatment with anti-gliotic agents such as chondroitinase ABC to induce improvement in the synaptic plasticity and regeneration parameters (e.g. Bradbury E J et al., Nature. 11; 416(6881): 636-40, 2002; and Barritt A W et al., J Neurosci. 18; 26(42):10856-67, 2006).

Hydrated gels (hydrogels) are viscous, semisolid entities at physiological temperatures and pH which can be used for tissue engineering and regenerative medicine. For example, hyaluronic acid-based hydrogels provide a growth supportive milieu for cells and tissues such as for nerve regeneration (Suzuki et. al., 2003; Itoh et. al., 2005), while guiding migration and regeneration of nutritional-trophic and anti-oxidative agents.

International Patent Application Publication No. WO2009/022339 discloses the use of a hyaluronic acid-based hydrogel containing the anti-oxidant sodium dismutase and a laminin peptide for neural tissue regeneration and repair.

SUMMARY OF THE INVENTION

According to an aspect of some embodiments of the present invention there is provided a composition comprising a hyaluronic acid, a laminin polypeptide, an antioxidant and an anti-gliotic agent.

According to an aspect of some embodiments of the present invention there is provided a method of generating a hydrogel, the method comprising:
(i) suspending a composition comprising a hyaluronic acid, a laminin polypeptide and an antioxidant in water so as to obtain a suspension which comprises at least 40% water; and
(ii) adding an anti-gliotic agent to the suspension,
thereby generating the hydrogel.

According to some embodiments of the invention, the antioxidant is superoxide dismutase (SOD).

According to some embodiments of the invention, the SOD comprises the amino acid sequence set forth by SEQ ID NO: 4.

According to some embodiments of the invention, the laminin polypeptide is set forth by SEQ ID NO: 1.

According to some embodiments of the invention, the antioxidant is superoxide dismutase (SOD) comprising the amino acid sequence set forth by SEQ ID NO: 4 and the laminin polypeptide is set forth by SEQ ID NO: 1.

According to some embodiments of the invention, the anti-gliotic agent is selected from the group consisting of anti-nogo A and Chondroitinase ABC.

According to some embodiments of the invention, the laminin polypeptide is set forth by SEQ ID NO: 1 and the anti-gliotic agent comprises anti-nogo A.

According to some embodiments of the invention, the laminin polypeptide is set forth by SEQ ID NO: 1 and the anti-gliotic agent comprises Chondroitinase ABC.

According to some embodiments of the invention, the hyaluronic acid, the antioxidant and the laminin polypeptide are cross linked.

According to some embodiments of the invention, there is provided matrix comprising the composition of the present invention.

According to some embodiments of the invention, there is provided a hydrogel comprising the composition of the present invention.

According to some embodiments of the invention, the hyaluronic acid is provided at a concentration range of about 0.5-1.5% in the hydrogel.

According to some embodiments of the invention, the laminin polypeptide is provided at a concentration range of about 20-100 µg/ml in the hydrogel.

According to some embodiments of the invention, the antioxidant is provided at a concentration range of about 5-40 µg/ml in the hydrogel.

According to some embodiments of the invention, the hyaluronic acid, the laminin polypeptide and the antioxidant are provided at a total concentration of about 0.01-0.6%.

According to some embodiments of the invention, the hyaluronic acid, the laminin polypeptide and the antioxidant are provided at a total concentration of about 0.4%.

According to some embodiments of the invention, the anti-gliotic agent is provided at a concentration range of about 5-300 µg/ml in the hydrogel.

According to some embodiments of the invention, there is provided a method of inducing formation or regeneration of a neuronal tissue in a subject in need thereof, the method comprising implanting the composition, the matrix or the hydrogel of the present invention in the subject, thereby inducing the formation or regeneration of the neuronal tissue in the subject.

According to some embodiments of the invention, there is provided a method of treating nerve injury in a subject in need thereof, the method comprising implanting the composition, the matrix or the hydrogel of the present invention at or near the nerve injury of the subject, thereby treating the nerve injury in the subject.

According to some embodiments of the invention, there is provided a method of preventing or treating neurogenic shock following nerve injury in a subject in need thereof, the method comprising implanting the composition, the matrix or the hydrogel of the present invention at or near the nerve injury of the subject, thereby preventing or treating the neurogenic shock in the subject.

According to some embodiments of the invention, the implanting is effected within 48 hours following the nerve injury.

According to some embodiments of the invention, the nerve injury is part of the central nervous system (CNS).

According to some embodiments of the invention, the nerve injury comprises spinal cord injury (SCI).

According to some embodiments of the invention, the nerve injury comprises traumatic brain injuries (TBI) or traumatic optic neuropathy (TON).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
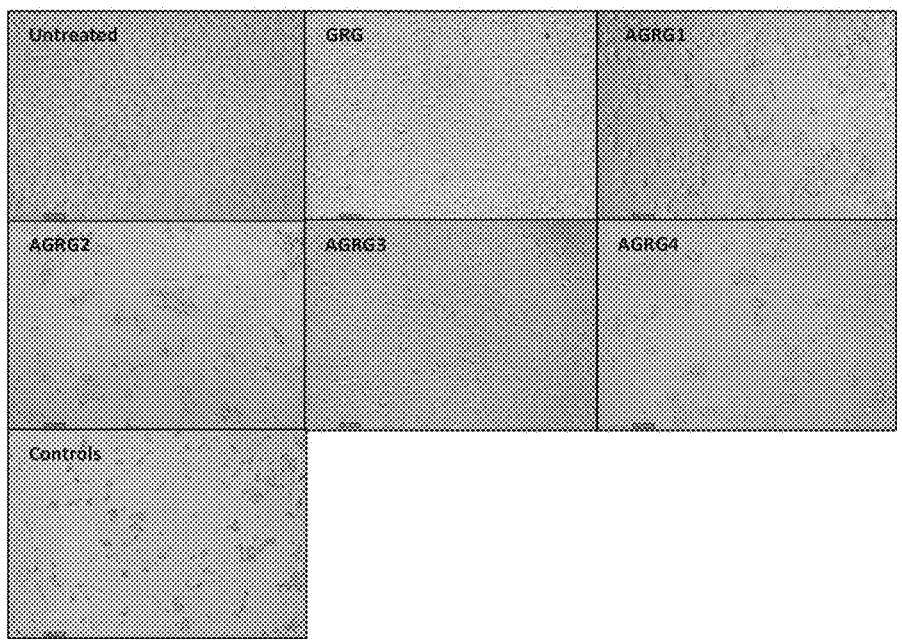

FIG. 1 shows photomicrographs of neuronal cell cultures treated with several anti-gliotic guiding regenerative gels (AGRGs) as compared to untreated cells and cells treated with guiding regenerative gel (GRG) alone or with anti-gliotic agents. Magnification X20. Morphological evaluation of the cells indicated that treatment with AGRG3 (GRG+anti nogo A) resulted in the highest number and density of neuronal cells; followed by AGRG1 (GRG+Chondroitinase ABC), AGRG2 (GRG+Mitomycin c) and AGRG4 (GRG+Chondroitinase ABC+mitomycin c+anti nogo A). Treatment with the three anti-gliotic agents (Chondroitinase ABC+mitomycin c+anti nogo A, denoted as control) resulted in a poor amount of neuronal cells.

Figure 2A:
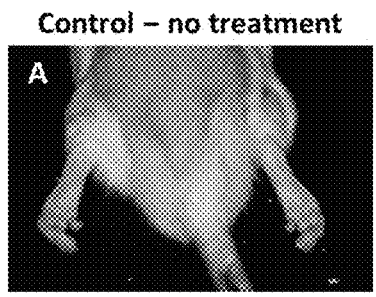
Figure 2B:
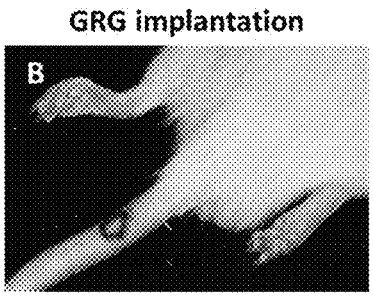
Figure 2C:

FIGS. 2A-C show representative photographs of Basso-Beattie-Bresnahan (BBB) functional evaluation of rat limbs 60 days post spinal cord injury (SCI). FIG. 2A demonstrates no movement in an untreated control rat (score 0). FIG. 2B demonstrates slight movement in a rat implanted with GRG (score 2). FIG. 2C demonstrates active movement of two joints and slight movement of the third joint in the previously paralyzed limb in a rat implanted with AGRG3 (GRG+anti-nogo A) (SCORE 6).

Figure 3:
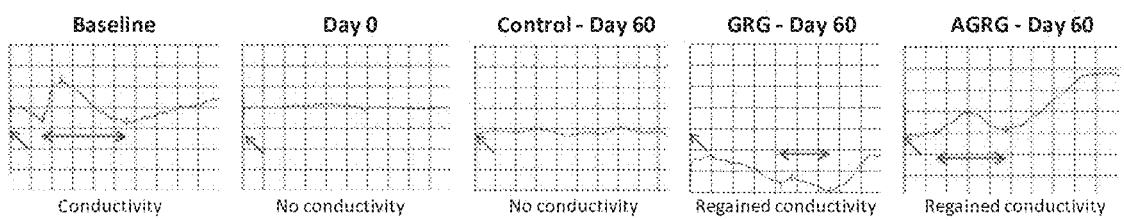

FIG. 3 shows representative graphs of somatosensory evoked potentials (SSEP) in the SCI rat model demonstrating that implantation of AGRG3 (GRG+anti-nogo A) resulted in regained conductivity. Shown are: SSEP before the SCI (baseline), immediately after (Day 0) and 60 days post SCI. The black arrows indicate the stimulus and the red arrows indicate the evoked potential.

Figure 4:
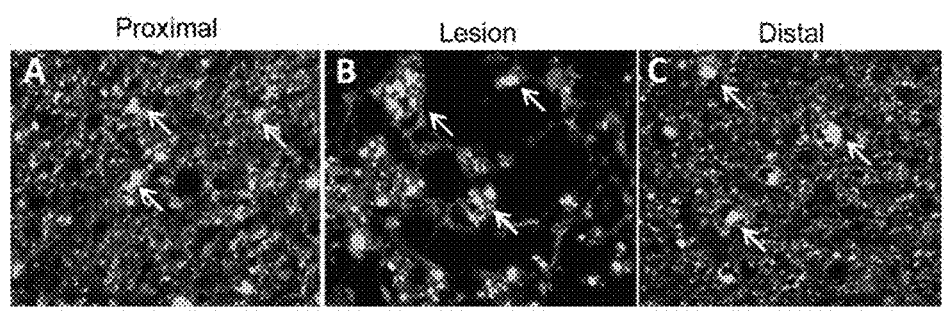

FIG. 4 shows representative histological photomicrographs demonstrating axonal sprouting in SCI rats implanted with AGRG3 (GRG+anti-nogo A). Magnification X40. Shown are cross sections of the proximal, lesion and distal parts, obtained from a rat implanted with AGRG3 and stained with NF. Arrows indicate few of the observed neuronal fibers; axonal sprouting is viewed as bright color.

Figure 5:
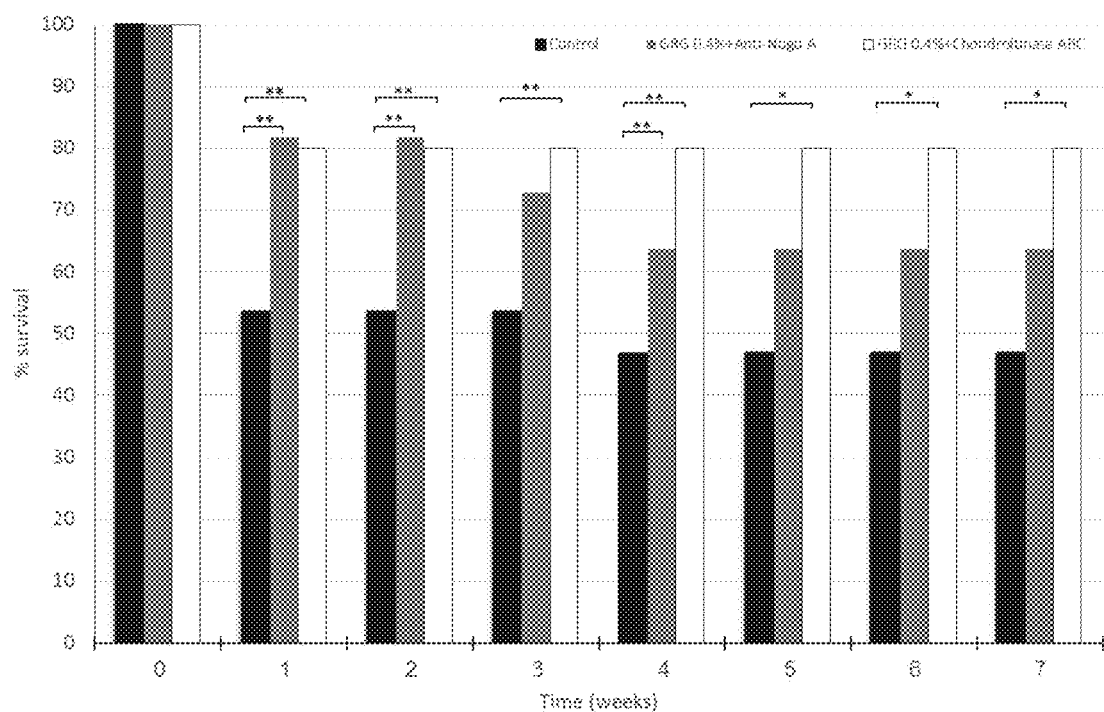

FIG. 5 shows a table and a graph summarizing survival rates (in percentages) of SCI rats implanted with AGRG (GRG+anti-nogoA, GRG+Chondroitinase ABC) as compared to control untreated SCI rats. * $P<0.05$ versus control; ** $P<0.1$ versus control.

DESCRIPTION OF SPECIFIC EMBODIMENTS OF THE INVENTION

The present invention, in some embodiments thereof, relates to combined treatment for nerve injury.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have designed a combined therapy for the treatment of nerve injury and prevention or treatment of neurogenic shock following nerve injury. The combined treatment is based on a co-treatment with hyaluronic acid, an antioxidant, a laminin peptide (SEQ ID NO: 1) and an anti-gliotic agent (e.g. Chondroitinase ABC, Anti-Nogo A), which is capable of supporting regeneration of neuronal tissue. When formulated as a gel the formulation is referred to as AGRG for anti-gliotic guiding regenerative gel.

As is illustrated hereinunder and in the Examples section, which follows, the present inventors demonstrate that treatment with AGRGs comprising Chondroitinase ABC or anti-Nogo A as the anti-gliotic component increase the survival and quality of neuronal cells in-vitro, an effect not achieved by treatment with GRG alone [i.e., hyaluronic acid, antioxidant and a laminin peptide (SEQ ID NO: 1)] or with the anti-gliotic agents alone (Example 2, FIG. 1). Moreover, the inventors demonstrate that implanting AGRG composed of GRG and anti-nogo A at or near the site of spinal cord injury (SCI) promoted nerve regeneration in a SCI rat model; and specifically improved movement, promoted regaining of conductivity in the previously paralyzed limbs, and promoted axonal penetration through the glial scar barrier (Example 4, FIGS. 2A-C, 3 and 4). In addition, the inventors demonstrate that AGRG composed of GRG and anti-nogo A or Chondroitinase ABC had a protective effect against spinal shock and decreased the mortality rate in the SCI treated rats (Example 6, FIG. 5).

Thus, according to a first aspect of the present invention, there is provided a composition comprising a hyaluronic acid, a laminin polypeptide, an antioxidant and an anti-gliotic agent.

As used herein, the term "hyaluronic acid (HA)", also known as hyaluronan, hyaluronate, refers to an unsulphated glycosaminoglycan composed of repeating disaccharide units of N-acetylglucosamine (GlcNAc) and glucuronic acid (GlcUA) linked together by alternating beta-1, 4 and beta-1, 3 glycosidic bonds. According to specific embodiments the hyaluronic acid is Na-HA. According to specific embodiments, the hyaluronic acid has a molecular weight from about $10^4$ Daltons to about $3 \times 10^6$ Daltons. The molecular weight of HA can be evaluated by e.g. viscosity measurement with a digital viscosimeter Brookfield brand Cone/Plate DVII+Per (Brookfield Engineering Laboratories Inc. Middleboro, Mass. 02346-1031 USA). The molecular weight of HA can be calculated as well by the discrepancy between the figure obtained in Dische's assays versus the data obtained by Park-Johnson (Park J. T. Johnson M. J. A submicrodetermination of glucose J. Biol. Chem. 181, 149-151, 1949) determination for reducing sugars.

The hyaluronic acid described herein includes naturally occurring HA synthetic HA or a combination of same. According to specific embodiments, the hyaluronic acid can be extracted and isolated from an organism such as rooster combs or umbilical cords or from bacterial cultures such as those of hemolytic group A or C Streptococci, or can be synthetically produced using methods which are well known in the art.

According to specific embodiments of the invention, the hyaluronic acid is pure enough from chemical or biological constituents so that it is biologically inert having a low rate of reactivity with other substances under ordinary conditions.

According to specific embodiments of the invention, the hyaluronic acid is pure enough so that it is biocompatible, e.g., when in contact with cells, tissues or body fluid of an organism does not induce adverse effects such as immunological reactions and/or rejections, cellular death, and the like.

According to specific embodiments, the hyaluronic acid is at least 80%, at least 90%, at least 95%, at least 98% or at least 99% pure. According to specific embodiments, the hyaluronic acid is analytical (i.e. 99.5%-100%) or pharmaceutical grade (98%-100% hyaluronic acid.

The hyaluronic acid described herein is capable of forming highly hydrated gels in aqueous solutions.

Total content of HA in the composition of the present invention can be determined by methods known in the art such as, but not limited to the content of uronic acids (lucuronic acid) by the routine test of Dische (Dische Z. A new specific color reaction of hexuronic Acids. J. Biol. Chem, 167, 189-197, 1947) employing the carbazol reagent.

As used herein the term "laminin" refers to the family of extracellular matrix glycoproteins, which form the major noncollagenous constituent of basement membrane. Laminins have been implicated in a wide variety of biological processes including cell adhesion, differentiation, migration, signaling, neurite outgrowth and metastasis. Laminins are composed of 3 non identical chains: laminin alpha, beta and gamma, each encoded by a distinct gene.

As used herein the phrase "laminin polypeptide" refers to an amino acid sequence which comprises at least 4 consecutive amino acids of a laminin polypeptide and which exhibits a biological activity (e.g., support cell survival, growth, proliferation, differentiation and/or migration).

According to some embodiments of the invention the laminin polypeptide can include an amino acid sequence of a laminin alpha-chain such as LAMA1 (e.g., GenBank Accession No. NP_005550.2), LAMA2 (e.g., GenBank Accession Nos. NP_000417.2 and NP_001073291.1), LAMA3 (e.g., GenBank Accession Nos. NP_937762.1 and NP_000218.2), LAMA4 (e.g., GenBank Accession Nos. NP_001098677.1, NP_001098676.1, NP_002281.2, NP_001098679.1, and NP_001098678.1), and LAMA5 (e.g., GenBank Accession No. NP_005551.3); a laminin beta-chain such as LAMB1 (e.g., GenBank Accession No. NP_002282.1), LAMB2 (e.g., GenBank Accession No. NP_002283.3), LAMB3 (e.g., GenBank Accession Nos. NP_000219.2 and NP_001017402.1) and LAMB4 (e.g., GenBank Accession No. NP_031382.2); and/or a laminin gamma-chain such as LAMC1 (e.g., GenBank Accession No. NP_002284.3), LAMC2 (e.g., GenBank Accession Nos. NP_005553.2 and NP_061486.2) and LAMC3 (e.g., GenBank Accession No. NP_006050.3).

According to specific embodiments of the invention, the laminin polypeptide includes a repeated amino acid sequence (e.g., a 4 or 5 amino acid repeated sequence) of a laminin sequence.

Non-limiting examples of laminin polypeptides which can be included in the composition of the invention include the peptides set forth in SEQ ID NOs: 1, 2 or 3. [KSIKVAVRSYIGSRCV (SEQ ID NO: 1), IKVAV (SEQ ID NO:2), YIGSR (SEQ ID NO:3)].

According to specific embodiments, the laminin polypeptide is set forth by SEQ ID NO: 1 (KSIKVAVRSYIGSRCV).

According to specific embodiments the laminin polypeptide is 5-50, 5-25, 5-20, 16-50 or 16-25 amino acids long.

According to specific embodiments, the laminin polypeptide is at least 16 amino acids long but shorter than 50 amino acids long.

The terms "polypeptide" or "peptide" which are interchangeably used herein, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |

TABLE 2-continued

| Non-conventional amino acid | Code | Non-conventional amino acid | Code |
|---|---|---|---|
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclization does not severely interfere with peptide characteristics, cyclic forms of the peptide can also be utilized.

Since the present peptides can be utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

In cases where large amounts or long polypeptides (e.g., longer than 20 amino acids) are desired, the polypeptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The composition further comprises an antioxidant which can protect cells or macromolecules (e.g., the polysaccharide) from oxidative stress (oxidative damage caused by free radicals). Thus, the antioxidant can extend the survival of the macromolecules by preventing their oxidative depolymerization.

Non-limiting examples of suitable antioxidants include molecules such as glutathione, vitamin C (sodium ascorbate), vitamin E (tocopherols and tocotrienols), N-Ac-L-cysteine, hydroquinone, glutamate, or enzymes such as catalase, superoxide dismutase, glutathione peroxidase or other peroxidases, and glucose-6-phosphate dehydrogenase (G6PD) (see Osmen I., Naziroglu M., Okutan R. Comparative study of antioxidant enzymes in tissues surrounding implant in rabbits. Cell. Biochem. Funct. 24:275-281, 2006).

According to specific embodiments, the antioxidant is superoxide dismutase (SOD).

As used herein, the term "superoxide dismutase" E.C. No: 1.15.1.1 refers to an enzyme that alternately catalyzes the dismutation (or partitioning) of the superoxide ($O_2^-$) radical into either ordinary molecular oxygen ($O_2$) or hydrogen peroxide ($H_2O_2$). Superoxide dismutase, in addition to its known activity as an antioxidant, can also serve as an anti-inflammatory agent when used in vivo. Non-limiting examples of superoxide dismutase (SOD) enzymes which can be used in the composition of the invention include, SOD-1 (soluble), SOD-2 (mitochondrial) or SOD-3 (extracellular), such as Homo sapiens soluble superoxide dismutase 1 (SOD-1) GenBank Accession No. NP_000445 (SEQ ID NO: 4); Homo sapiens mitochondrial superoxide dismutase 2 (SOD-2) GenBank Accession Nos. NP_001019637.1 (isoform B), NP_001019636.1 (isoform A), NP_000627.2 (isoform A); Homo sapiens extracellular superoxide dismutase 3 (SOD-3) GenBank Accession No. NP_003093.2; Saccharomyces cerevisiae SOD-1 GenBank Accession No. NP_012638.1; and Rattus norvegicus SOD-1 GenBank Accession No. NP_058746.

According to specific embodiments, the SOD comprises the amino acid sequence set forth by SEQ ID NO: 4.

The antioxidant of the invention can be produced by recombinant techniques, e.g. as described in Hartman J R., et al., 1986 (Proc. Natl. Acad. Sci. USA, Vol: 83, pp 7142-7146). For example, a polynucleotide encoding superoxide dismutase 1 (GenBank Accession No. NM_000454; SEQ ID NO: 5) can be ligated into a nucleic acid construct suitable for expression in a host cell (e.g., bacterial cell, yeast cell, mammalian cell). Such a nucleic acid construct includes a promoter sequence for directing transcription of the polynucleotide sequence in the cell in a constitutive or inducible manner, and may also include sequences which render this vector suitable for replication and integration in prokaryotes, eukaryotes, or preferably both (e.g., shuttle vectors); transcription and translation initiation sequence, enhancers, transcription and translation terminator, and a polyadenylation signal which may increase the efficiency of mRNA translation; a signal sequence for secretion; sequences engineered to enhance stability, production, purification, yield or toxicity of the expressed polypeptide.

The antioxidant can be recovered and purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromate-focusing and differential solubilization.

According to specific embodiments of the invention, the antioxidant is retrieved so that it is pure enough from chemical or biological constituents to allow for the effective use of the recombinant polypeptide as an antioxidant. Activity of the anti-oxidant, e.g. SOD, may be determined by methods well known in the art and include measurement at 560 nm as the rate of suppression of reduction of nitrotetrazolium blue when superoxide anion radical was generated during oxidation of xanthine by xanthine oxidase.

According to specific embodiments, the anti-oxidant (e.g. SOD) is at least 80%, at least 90%, at least 95%, at least 98% or at least 99% pure.

According to specific embodiments, the anti-oxidant (e.g. SOD) is analytical or pharmaceutical grade anti-oxidant.

As used herein, the term "gliosis" refers to a nonspecific change of glial cells e.g. astrocytes and macrophages, in response to damage to the central nervous system (CNS). Typically, gliosis involves proliferation of glial cell, hypertrophy of glial cells and secretion of connective tissue matrix substances such as proteoglycans (PGs), collagens and myelin-derived residues. Gliosis, in its extreme form, leads to the formation of a scar tissue in the CNS comprising dense fibrous network of glial cell in areas of damage resulting in inhibition of axons sprouting and restricting neuronal regeneration.

Methods of determining gliosis are known in the art and are further described in the Examples section which follows and include in-vitro methods determining neuronal cells survival and astrocytes survival and quality, biosynthesis and accumulation of inhibitory intracellular, pericellular and extracellular (ECM) components such as GAGs; and in-vivo methods determining neuronal regeneration in response to CNS injury e.g. SCI.

As used herein, the term "anti-gliotic agent" refers to an agent capable of decreasing the extent of gliosis. Typically, an anti-gliotic agent decreases the extent of gliosis by degrading the scar barrier and/or inhibiting its further formation. According to specific embodiments the decrease is at least 1.05 fold, at least 1.1 fold, at least 1.2 fold, at least 1.3 fold, at least 1.4 fold, 1.5 fold, at least 2 fold, at least 3 fold, at least 5 fold, at least 10 fold, or at least 20 fold as compared to same in the absence of the anti-gliotic agent.

According to other specific embodiments the decrease is by at least 5%, by at least a 10%, at least 20%, at least 30%, at least 40% or at least 50% as compared to same in the absence of the anti-gliotic agent.

According to specific embodiments, the composition comprises at least one anti-gliotic agent.

According to specific embodiments, the composition comprises one anti-gliotic agent. According to other specific embodiments, the composition comprises several distinct (e.g. 2, 3, 4, 5) anti-gliotic agents.

According to a specific embodiment, the anti-gliotic agent is an antibody directed to a gliotic protein i.e., participating in the gliotic process.

According to another specific embodiment, the anti-gliotic agent is an enzyme which can ameliorate the gliotic process.

According to another specific embodiment, the anti-gliotic agent is a peptide which can ameliorate the gliotic process.

According to another specific embodiment, the anti-gliotic agent is a growth factor which can ameliorate the gliotic process.

According to another specific embodiment, the anti-gliotic agent is a small molecule which can ameliorate the gliotic process.

According to another specific embodiment, the anti-gliotic agent is a polynucleotide molecule which can ameliorate the gliotic process.

Non limiting examples of anti-gliotic agents include Chondroitinase ABC (E.C. No 4.2.2.4), β-D-xyloside (E.C. No 217.897.1), Collagenase Type I (E.C. No 232-582-9, Mitomycin-C (CAS No 50-07-7), MMP-3-Matrix Metalloproteinase (E.C. No 3.4.24, anti Nogo A, anti-TGFβ 1, 2 & 3, angiotensin Converting Enzyme (ACEa, E.C No 3.4.15.1), anti NG-2-domain, Decorin (e.g. human Decorin such as Uniprot accession No. P07585, PAPN-beta aminopropionyl, Mannose-6-phosphate (CAS No 3672-15-9), Oxidized recombinant human galectin-1, Copaxone (glatiamer acetate) and Tri peptide (ser-gly-gly).

According to specific embodiments, the anti-gliotic agent is selected from the group consisting of anti-nogo A and Chondroitinase ABC.

According to specific embodiments, the anti-gliotic agent comprises anti-nogo A.

As used herein the term "nogo A" also known as Reticulon 4, Neuroendocrine-Specific Protein, Neurite Outgrowth Inhibitor, NOGO, Neurite Growth Inhibitor 220 refers to an expression product e.g. protein of the RTN4 gene. According to specific embodiments, the nogo A protein refers to the human protein, such as provided in the following GenBank Numbers NP_008939, NP_065393, NP_722550, NP_997403 and NP_997404.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

According to specific embodiments, the antibody is a monoclonal antibody.

According to other specific embodiments, the antibody is a polyclonal antibody.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

According to specific embodiments, the antibody is a human or a humanized antibody.

Methods for producing human antibodies and humanizing non-human antibodies are well known in the art.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Anti-nogo A antibodies which can be used with specific embodiments of the invention are known in the art and can be commercially obtained from e.g. Biotest Ltd., Abcam and EMD Millipore.

According to other specific embodiments, the anti-gliotic agent comprises Chondroitinase ABC.

As used herein, the term "Chondroitinase ABC" E.C. No 4.2.2.4, also known as Chondroitin ABC lyase, chondroitinase and chondroitin ABC eliminase refers to an enzyme which acts on chondroitin 4-sulfate, chondroitin 6-sulfate and dermatan sulfate and catalyzes the following reaction: Eliminative degradation of polysaccharides containing 1,4- beta-D-hexosaminyl and 1,3-beta-D-glucuronosyl or 1,3-alpha-L-iduronosyl linkages to disaccharides containing 4-deoxy-beta-D-gluc-4-enuronosyl groups.

This enzyme acts on chondroitin 4-sulfate, chondroitin 6-sulfate and dermatan sulfate.

Chondroitinase ABC can be commercially obtained from e.g. Sigma and R&D Systems.

According to specific embodiments, there is provided a composition comprising a hyaluronic acid, a laminin polypeptide as set forth by SEQ ID NO: 1, an antioxidant and an anti-gliotic agent, said anti-gliotic agent comprises anti-nogo A.

According to specific embodiments, there is provided a composition comprising a hyaluronic acid, a laminin polypeptide as set forth by SEQ ID NO: 1, an antioxidant and an anti-gliotic agent, said anti-gliotic agent comprises Chondroitinase ABC.

According to specific embodiments, the components of the composition are cross-linked.

According to specific embodiments, the hyaluronic acid, the antioxidant and the laminin peptide of the composition are cross-linked.

Cross-linking (i.e., binding via covalent or ionic bonds) of the components comprised in the composition can be performed using any cross-linking or coupling agent known in the art. Basically the principles of cross linking is combining free primary amino groups with carboxyl groups, or oxidizing in between close hydroxyl groups, forming reactive aldehydes, to interact either among themselves or with amines of additional conjugate may be formed via tiol residues.

According to specific embodiments, cross-linking does not affect the biological activities of the bonded elements.

Non-limiting examples of suitable cross-linking agents include dimethyl suberimidate (an imidoester cross linker); Bis(Sulfosuccinimidyl) suberate (BS3; an NHS-ester cross linker); formaldehyde; 1-Ethyl-3-[3-dimethylaminopropyl] carbodiimide hydrochloride (EDC; the carbodiimide cross linker); N-hydroxyuccinimide (NHS) [Mao J. S, et al., Biomaterials. 24, 1621-1629, 2003; Choi Y. S., et al., J. Biomed. Mater. Res. 48,631-639, 1999; Richert L., et al., Biomacromolecules, 5, 284-294, 2004)]; Divinyl sulfone (DVS); and genipin [Sung H. W., et al., J Biomed. Mater. Res. A, 64A:427-438, 2003; Chen S C., et al., J. Control Release. 96, 285-300, 2004; Mwale F., et al., Tissue Eng., 11, 130-40, 2005; Chen H., et al., Biomacromolecules, 7, 2091-2098, 2006]. For ex vivo or in vivo cross-linking photo-reactive amino acid analogs (e.g., diazirine analogs to leucine and methionine) can be added to the composition and following exposure to ultraviolet light, the diazirines are activated and bind to interacting side chains (e.g., carboxyl or amino groups).

According to specific embodiments of the invention, cross-linking is performed using a non-toxic and/or biocompatible agent. Examples include, but are not limited to 3-dimenthy-aminoprophyl)-N-ethyl carbodiimide (EDC-N; Sigma-Aldrich-Fluka, St Louis, Mo. 63178, Catalogue No. 03459), divinyl sulfone (DVS; Sigma, Catalogue No. V-370-0) and genipin (Sigma Catalogue No. G-4796).

Thus, according to specific embodiments, there is provided a composition as disclosed herein wherein the hyaluronic acid, the antioxidant and the laminin polypeptide are cross linked.

According to other specific embodiments, there is provided a composition as disclosed herein wherein the hyaluronic acid, the laminin polypeptide and the anti-gliotic agent are cross linked.

According to specific embodiments, the composition described herein has combined improved activity on neural cells survival, neuronal regeneration and/or prevention of glial scar tissue growth. As used herein the phrase "combined improved activity" refers to at least additive but preferably synergistically improved activity.

It should be noted that since the components comprised in the composition of the invention can be prepared using synthetic or recombinant techniques they are obtainable sterile preparations of analytical or pharmaceutical grade.

As mentioned above, the present inventors have generated a novel hydrogel from a hyaluronic acid, a laminin polypeptide (SEQ ID NO: 1), an antioxidant (superoxide dismutase) and an anti-gliotic agent (e.g. anti-nogo A, Chondroitinase ABC).

Thus, according to specific embodiments of the invention, there is provided a hydrogel comprising the composition described herein.

According to another aspect of the present invention, there is provided a method of generating a hydrogel, the method comprising:

(i) suspending a composition comprising a hyaluronic acid, a laminin polypeptide and an antioxidant in water so as to obtain a suspension which comprises at least 40% water; and (ii) adding an anti-gliotic agent to said suspension, thereby generating the hydrogel.

According to specific embodiments, step (i) is effected according to the teachings of International Patent Application Publication No. WO2009/022339, the contents of which are incorporated herein in their entirety.

As used herein, the term "hydrogel" refers to a material comprising the composition of some embodiment of the invention and water, in which the water constitutes more than 40%.

According to specific embodiments of the invention, the hydrogel comprises at least about 50%, at least about 60% water, at least about 70% water, at least about 80% water, at least about 90% water, at least about 95% water, at least about 96% water, at least about 97% water, at least about 98% water, at least about 99% water.

According to specific embodiments, the hydrogel is viscous (e.g. approximately 0 cP during no movement and 110-130 cP during movement).

According to specific embodiments, the hydrogel is transparent.

According to specific embodiments, the hyaluronic acid is provided at a concentration range of about 0.3-2%, e.g., about 0.4-1.8%, e.g., about 0.5-1.6, e.g., about 0.5-1.5%, e.g., about 0.6-1.4%, e.g., about 0.8-1.2%, e.g., about 1.2% in the composition e.g. hydrogel.

According to a specific embodiment, the hyaluronic acid is provided at a concentration range of about 0.5-1.5% in the composition e.g. hydrogel.

According to some embodiments, the laminin polypeptide (e.g., SEQ ID NO: 1) is provided at a concentration range of about 10-200 µg/ml, e.g., about 20-100 µg/ml, e.g., about 50 µg/ml in the composition e.g. hydrogel.

According to a specific embodiment, the laminin polypeptide is provided at a concentration range of about 20-100 µg/ml in the composition e.g. hydrogel.

According to some embodiments of the invention, the antioxidant (e.g. superoxide dismutase) is provided at a concentration range of about 8 µM (about 0.25 microgram/ml) to 8 mM (about 250 microgram/ml) in the hydrogel. For example, the antioxidant (e.g. superoxide dismutase) can be provided at a concentration range of about 0.5 µg/ml to about 200 µg/ml, e.g., from about 1 µg/ml to about 100 µg/ml, e.g., from about 2 µg/ml to about 80 µg/ml, e.g., from about 4 µg/ml to about 40 µg/ml, e.g., from about 5 µg/ml to about 50 µg/ml, e.g., from about 10 µg/ml to about 50 µg/ml, e.g., from about 15 µg/ml to about 40 µg/ml, e.g., from about 20 µg/ml to about 30 µg/ml, e.g., about 25 µ/ml.

According to specific embodiments, the antioxidant is provided at a concentration range of about 5-40 µg/ml in the composition e.g. hydrogel.

According to specific embodiments, the ratio between the hyaluronic acid, the laminin polypeptide and the antioxidant in the composition e.g. hydrogel is between HA 0.01 mg: laminin polypeptide 50 µg: SOD 250 µg per ml to HA 1.2 mg: laminin polypeptide 50 µg: SOD 250 µg per ml.

According to a specific embodiment, the ratio between the hyaluronic acid, the laminin polypeptide and the antioxidant in the composition e.g. hydrogel is approximately HA 0.4 mg: laminin polypeptide 50 µg: SOD 250 µg per ml.

According to specific embodiments, the hyaluronic acid, the laminin polypeptide and the antioxidant are provided at a total concentration of about 0.01-0.6%.

According to specific embodiments, the hyaluronic acid, the laminin polypeptide and the antioxidant are provided at a total concentration of about 0.02-0.5%.

According to specific embodiments, the hyaluronic acid, the laminin polypeptide and the antioxidant are provided at a total concentration of about 0.4%.

According to specific embodiments, the hyaluronic acid, the laminin polypeptide and the antioxidant are provided at a total concentration of about 0.02%.

According to specific embodiments, the anti-gliotic agent is provided at a concentration range of about 5-300 µg/ml in the composition e.g. hydrogel.

According to some embodiments of the invention, the method further comprises cross-linking the composition. Methods and agents that can be used for cross-linking are well known in the art and were further described hereinabove.

According to specific embodiments of the invention, the hydrogel is lyophilized by methods well known in the art such that a dry matrix is obtained.

According to specific embodiments, the dry mix comprises less than 50%, less than 30%, less than 10%, less than 5%, less than 2%, less than 1%, or less than 0.5% water. It should be noted that water-free matrices can be preserved for long periods of time without being subjected to enzymatic degradation or contamination (e.g., by microorganisms).

Thus, according to specific embodiments, there is provided a matrix comprising the composition described herein.

As used herein the phrase "matrix" refers to a two-dimensional or a three-dimensional scaffold (also referred to herein as supporting framework) comprising the composition of the invention. The scaffold may further provide mechanical stability and support.

The matrix can be kept in a dry or wet form, or can be frozen according to the intended use.

According to specific embodiments, the dry matrix can be further hydrated in an aqueous solution (e.g., water) until a hydrogel is formed.

According to specific embodiments, the dimensions of the matrix vary according with the lesion (e.g. nerve injury e.g. spinal cord injury) to be treated. For example, the size of the matrix can be smaller than or substantially the same size as the lesion to be treated. Alternatively, the size of the matrix can be larger than the lesion.

Scaffold material may comprise natural or synthetic organic polymers that can be gelled, or polymerized or solidified (e.g., by aggregation, coagulation, hydrophobic interactions, or cross-linking) into a two-dimensional or a three-dimensional structure.

The scaffold of the present invention may be made uniformly of a single polymer, co-polymer or blend thereof. However, it is also possible to form a scaffold according to the invention of a plurality of different polymers. There are no particular limitations to the number or arrangement of polymers used in forming the scaffold. Any combination which is biocompatible, may be formed into fibers, and degrades at a suitable rate, may be used.

Both the choice of polymer and the ratio of polymers in a co-polymer may be adjusted to optimize the stiffness of the scaffold. The molecular weight and cross-link density of the scaffold may also be regulated to control both the mechanical properties of the scaffold and the degradation rate (for degradable scaffolds). The mechanical properties may also be optimized to mimic those of the tissue at the implant site.

Polymers used in scaffold material compositions may be biocompatible, biodegradable and/or bioerodible and may act as adhesive substrates for cells. In exemplary embodiments, structural scaffold materials are easy to process into complex shapes and have a rigidity and mechanical strength suitable to maintain the desired shape under in vivo conditions.

In certain embodiments, the structural scaffold materials may be non-resorbing or non-biodegradable polymers or materials. Such non-resorbing scaffold materials may be used to fabricate materials which are designed for long term or permanent implantation into a host organism.

The phrase "non-biodegradable polymer", as used herein, refers to a polymer or polymers which at least substantially (i.e. more than 50%) do not degrade or erode in vivo. The terms "non-biodegradable" and "non-resorbing" are equivalent and are used interchangeably herein. Examples of biocompatible non-biodegradable polymers which are useful as scaffold materials include, but are not limited to, polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, and other similar compounds known to those skilled in the art.

In other embodiments, the structural scaffold materials may be a "bioerodible" or "biodegradable" polymer or material.

The phrase "biodegradable polymer" as used herein, refers to a polymer or polymers which degrade in vivo, and wherein erosion of the polymer or polymers over time occurs concurrent with or subsequent to release of the composition. The terms "biodegradable" and "bioerodible" are equivalent and are used interchangeably herein.

Such bioerodible or biodegradable scaffold materials may be used to fabricate temporary structures. Examples of biocompatible biodegradable polymers which are useful as scaffold materials include, but are not limited to, polylactic acid, polyglycolic acid, polycaprolactone, and copolymers thereof, polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and mixtures of such polymers. In still other embodiments, a mixture of non-biodegradable and bioerodible and/or biodegradable scaffold materials may be used to form a biomimetic structure of which part is permanent and part is temporary.

According to specific embodiments, PLA, PGA and PLA/PGA copolymers are used for forming the scaffolds of the present invention.

In an exemplary embodiment, scaffolds materials may comprise naturally occurring substances, such as, fibrinogen, fibrin, thrombin, chitosan, collagen, alginate, poly(N-isopropylacrylamide), albumin, collagen, synthetic polyamino acids, prolamines, polysaccharides such as alginate, heparin, and other naturally occurring biodegradable polymers of sugar units.

According to specific embodiments, the scaffolds of the present invention are porous. The porosity may be controlled by a variety of techniques known to those skilled in the art.

According to a specific embodiment of the present invention, the scaffolds are fabricated from synthetic biomaterials and are capable of conducting electricity and naturally eroding inside the body. In an exemplary embodiment, the scaffolds comprise a biocompatible polymer capable of conducting electricity e.g. a polypyrrole polymer. Polyaniline, polyacetyline, poly-p-phenylene, poly-p-phenylene-vinylene, polythiophene, and hemosin are examples of other biocompatible polymers that are capable of conducting electricity and may be used in conjunction with the present invention. Other erodible, conducting polymers are well known (for example, see Zelikin et al., Erodible Conducting Polymers for Potential Biomedical Applications, Angew. Chem. Int. Ed. Engl., 2002, 41(1):141-144). Any of the foregoing electrical conducting polymers can be applied or coated onto a malleable or moldable scaffold.

The scaffolds may be made by any of a variety of techniques known to those skilled in the art. Salt-leaching, porogens, solid-liquid phase separation (sometimes termed freeze-drying), and phase inversion fabrication may all be used to produce porous scaffolds. Fiber pulling and weaving (see, e.g. Vacanti, et al., (1988) Journal of Pediatric Surgery, 23: 3-9) may be used to produce scaffolds having more aligned polymer threads. Those skilled in the art will recognize that standard polymer processing techniques may be exploited to create polymer scaffolds having a variety of porosities and microstructures.

Scaffold materials are readily available to one of ordinary skill in the art, usually in the form of a solution (suppliers are, for example, BDH, United Kingdom, and Pronova Biomedical Technology a.s. Norway). For a general overview of the selection and preparation of scaffolding materials, see the American National Standards Institute publication No. F2064-00 entitled Standard Guide for Characterization and Testing of Alginates as Starting Materials Intended for Use in Biomedical and Tissue Engineering Medical Products Applications".

According to specific embodiments the scaffold comprises a biodegradable membrane e.g. a dura film such as Lyodura, AESCULAP.

According to specific embodiments of the invention, the hydrogel or the matrix further comprises ex-vivo seeded cells such as stem cells or differentiated cells (e.g. neuronal progenitor cells).

Non-limiting examples of stem cells which can be used by the invention include embryonic stem cells, induced pluripotent stem cells (iPS), neuronal progenitor cells, hematopoietic stem cells (e.g., bone marrow stem cells, cord blood cells, peripheral blood stem cells), adult stem cells and mesenchymal stem cells.

According to some embodiments of the invention, the stem cells are neuronal progenitor cells (such as those obtained from embryonic or fetal neuronal tissue or brain).

According to specific embodiments, the differentiated cells are neural cells.

As mentioned above and described in the Examples section which follows the present inventors have uncovered that a composition which comprises hyaluronic acid, a laminin polypeptide, a superoxide dismutase and an antigliotic agent (e.g., in a form of a hydrogel) can increase neuronal cells survival and support neuronal regeneration.

Thus, according to an aspect of some embodiments of the invention, there is provided a method of inducing formation or regeneration of a neuronal tissue in a subject in need thereof, the method comprising implanting the composition, the matrix or the hydrogel of the present invention in the subject, thereby inducing the formation or regeneration of the neuronal tissue in the subject.

As used herein, the term "subject" refers to a mammalian subject (e.g., human being) of any gender and any age including neonatal, infant, juvenile, adolescent, adult and elderly adult.

According to specific embodiments of the invention, the term encompasses individuals who suffer from a pathology (e.g. nerve injury, neurogenic shock) as described below.

According to specific embodiment, the subject is demonstrating symptom(s) characterizing the pathology.

Veterinary uses are also contemplated. Thus, according to specific embodiments, the components of the composition, the matrix and the hydrogel of the present invention are selected avoiding xeno responses.

According to another aspect of some embodiments of the invention, there is provided method of treating nerve injury in a subject in need thereof, the method comprising implanting the composition, the matrix or the hydrogel of the present invention at or near the nerve injury of the subject, thereby treating the nerve injury in the subject.

According to another aspect of some embodiments of the invention, there is provided the composition, the matrix or the hydrogel of the present invention for use in the treatment of nerve injury in a subject in need thereof.

As used herein the phrase "nerve injury" refers to any disorder, disease, or condition exhibiting damage (i.e., non-functioning tissue, cancerous or pre-cancerous tissue, broken tissue, fractured tissue, fibrotic tissue, or ischemic tissue) or loss (e.g., following a trauma, an infectious disease, a genetic disease, and the like) of neuronal tissue which requires tissue regeneration. According to specific embodiments the nerve injury is caused by trauma and not by a disease.

According to specific embodiments the neuronal tissue and/or the nerve injury is part of the central nervous system (CNS).

The term "central nervous system (CNS)", as used herein can refer to a subject's brain, spinal cord and/or optic nerve.

According to specific embodiments, the nerve injury comprises spinal cord injury.

As used herein, the phrase "spinal cord injury (SCI)" refers to an injury to the spinal cord that is caused by trauma and not by disease. Spinal cord injuries have many causes; according to specific embodiments, the SCI is caused by a major trauma from motor vehicle accidents, falls, sports injuries or violence. Depending on where the spinal cord and nerve roots are damaged, the symptoms can vary widely e.g. from pain to paralysis to incontinence. The SCIs can be incomplete or complete injury which means a total loss of function. According to specific embodiments, the SCI is complete SCI.

According to specific embodiments, the nerve injury comprises traumatic brain injury (TBI).

As used herein, the phrase "traumatic brain injury (TBI)" refers to brain injury caused by trauma and not by disease. TBIs have many causes; according to specific embodiment, the TBI is caused by falls, vehicle collisions, sports collisions or combats. The phrase includes both mild and severe TBI including closed-head injuries, concussions or contusions and penetrating head injuries.

According to specific embodiments, the nerve injury comprises traumatic optic neuropathy (TON).

As used herein, the phrase "traumatic optic neuropathy (TON)" refers to injury to the optic nerve caused by trauma and not by disease. According to specific embodiments, TON results in vision loss, which may be partial or complete. TONs have many causes; according to specific embodiments, the TON is caused by an anatomical disruption of the optic nerve fibers from penetrating orbital trauma, bone fragments within the optic canal or nerve sheath hematomas.

The phrase "treating" refers to inhibiting or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. According to specific embodiments, treating comprises increasing survival.

Thus, according to another aspect of some embodiments of the invention, there is provided a method of increasing survival following nerve injury in a subject in need thereof, the method comprising implanting the composition, the matrix or the hydrogel of the present invention at or near the nerve injury of the subject, thereby increasing survival of the subject.

According to another aspect of some embodiments of the invention, there is provided the composition, the matrix or the hydrogel of the present invention for use in increasing survival following nerve injury in a subject in need thereof.

According to specific embodiments the increase is at least 1.5 fold, at least 2 fold, at least 3 fold, at least 5 fold, at least 10 fold, or at least 20 fold as compared to same in the absence of implanting the composition, the matrix or the hydrogel of the present invention which may be obtained from databases and the known literature.

According to other specific embodiments the increase is by at least 5%, by at least a 10%, at least 20%, at least 30%, at least 40%, at least 50%, at least 60%, at least 70%, at least 80%, at least 90%, at least 95% or at least 100% as compared to same in the absence of implanting the composition, the matrix or the hydrogel of the present invention which may be obtained from databases and the known literature.

According to specific embodiments, the mortality associated with the pathology (e.g. nerve injury) is due to neurogenic shock.

Hence, according to another aspect of some embodiments of the invention, there is provided a method of preventing or treating neurogenic shock following nerve injury in a subject in need thereof, the method comprising implanting the composition, the matrix or the hydrogel of the present invention at or near the nerve injury of the subject, thereby preventing or treating the neurogenic shock in the subject.

According to another aspect of some embodiments of the invention, there is provided the composition, the matrix or the hydrogel of the present invention for use in preventing or treating neurogenic shock in a subject in need thereof.

As used herein, the term "preventing" refers to keeping a disease, disorder or condition from occurring in a subject who may be at risk for the disease, but does not yet display symptoms of the disease disorder or condition or has not yet been diagnosed as having the disease, disorder or condition. Those of skill in the art will understand that various methodologies and assays can be used to assess the development of a pathology.

As used herein, the phrase "neurogenic shock" refers to a shock resulting in low blood pressure, occasionally with a slowed heart rate that is attributed to the disruption of the autonomic pathways that occur following damage to the CNS (e.g. SCI). Methods of diagnosing neurogenic shock and evaluating its progression are known in the art and include, but not limited to, radiographic imaging, hemodynamic monitoring and/or clinical exam.

According to specific embodiments, the methods or compositions of the present invention prevent and/or treat at least one of the symptoms of neurogenic shock including, but not limited to, instantaneous hypotension due to sudden, massive vasodilation, warm, flushed skin due to vasodilation and inability to vasoconstrict, priapism, also due to vasodilation; inability to get tachycardic, bradycardia, diaphragmatic breathing due to loss of nervous control of the intercostal muscles (typically due to an injury below the 5th cervical vertebra), respiratory arrest immediately following the injury due to loss of nervous control of the diaphragm (typically due to an injury above the 3rd cervical vertebra), organ dysfunction or death.

According to specific embodiments, the methods or compositions of the present invention treat or prevent organ dysfunction or death resulting from neurogenic shock.

According to specific embodiments, the methods or compositions of the present invention treat a subject demonstrating at least one symptom of neurogenic shock, such as, but not limited to, the symptoms described hereinabove.

According to specific embodiments, the methods or compositions of the present invention treat a subject demonstrating at least one symptom of neurogenic shock selected from the group consisting of hypotension, bradycardia and diaphragmatic breathing.

Those of skills in the art are capable of determining when and how to implant the composition, the matrix or the hydrogel to thereby induce e.g. tissue formation within the subject. See for example, Artzi Z, et al., 2005, J. Clin. Periodontol. 32: 193-9; Butler C E and Prieto V G, 2004, Plast. Reconstr. Surg. 114: 464-73.

According to specific embodiments, the composition, the matrix or the hydrogel of the present invention are implanted locally at the site of the nerve injury.

For example, for treating spinal cord injuries, the composition, the matrix or the hydrogel is implanted directly into the lesion (e.g. into the epicenter of the injury), and near the lesion (e.g. at distance of approximately 0.5 cm from the injured site). Following implantation the implants can be fixed by surgical adhesives (e.g. BioGlue, CryoLife); and finally the muscular and cutaneous planes are closed and sutured.

According to specific embodiments, the composition, the matrix or the hydrogel is implanted within 12 hours, within 24 hours, within 48 hours, within 72 hours or within 96 hours following the nerve injury, each possibility represents a separate embodiment of the present invention.

According to specific embodiments, the composition, the matrix or the hydrogel is implanted within 48 hours following the nerve injury.

According to specific embodiments, the composition, the matrix or the hydrogel is implanted within 24 hours following the nerve injury.

The compositions, the matrix and/or the hydrogel of the invention may, if desired, be presented in a pack or dispenser device, such as an FDA approved kit, or an article of manufacture (with packaging material), which may contain one or more unit dosage forms containing the active ingredient. The pack may, for example, comprise metal or plastic foil, such as a blister pack. The pack or dispenser device may be accompanied by instructions for administration, implantation and/or treating a subject. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. The compositions, matrix or hydrogel of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

In-Vitro Effect of Anti-Gliotic Agents on Astrocytes Survival

Materials and Methods

Chemicals—Bt-cAMP (N6,2'-O-Dibutyryladenosine 3',5'-cyclic monophosphate, sodium salt, Sigma Catalog Number D0627, molecular weight 491.37) at a dose of 1 mM; and Theophylline (Theophylline anhydrous—1,3-Dimethylxanthine, Sigma Catalog Number T1633, molecular weight 180.2) at a dose of 0.25-0.5 mM were used for astrocytes activation.

The anti-gliotic agents used were:

Chondroitinase ABC from *Proteus vulgaris* (Sigma Catalog Number C2905). This is a glycosaminoglycans (GAGs) degrading enzyme which operates on the accumulated GAG in the glial scar.

β-D-xyloside (also denoted as p-nitrophenyl-beta-D-xylopyranoside or 4-Nitrophenyl β-D-xylopyranoside, Sigma Catalog Number C3667 or N2132, molecular weight 271.2). This is an artificial acceptor of GAG chains, replacing the natural acceptor i.e. the core protein, resulting in soluble, smaller molecular weight GAG chains that are found in the extracellular milieu in culture and drained out via the kidney in-vivo.

Collagenase Type I from *Clostridium histolyticum* (Sigma Catalog Number C0130). Collagen tends to accumulate in the glial scar, causing inhibition of neuronal growth and inhibiting fibers sprouting.

Mitomycin-C from *Streptomyces caespitosus* (Sigma Catalog Number M0503). This agent specifically eliminates astrocytes thereby diminishes glial reactivity.

MMP-3-Matrix Metalloproteinase, human Stromlysin STR1 (Sigma Catalog Number SRP 7783). This is an endoproteases aggrecanases, expressing catalytic activity which has a role in maintenance and remodeling of extracellular matrix (ECM), degrading GAGs, fibronectins, laminins and collagens; and preventing the synthesis of normal proteoglycans (PGs).

Rabbit Anti Nogo A, Recombinant (Enco Scientific Services LTD., Catalog number SC-25660). Nogo, a myelin derived residue, is a component of the CNS white matter that inhibits outgrowth.

Mouse anti-TGFβ 1,2 & 3 (Monoclonal mouse IgG clone #1011, Biotest Ltd, Kfar Saba, Israel, Catalog number MAR1835).

Angiotensin Converting Enzyme (ACE) Human recombinant (Biotest Ltd, Kfar Saba, Israel, Catalog number 929-ZN ACE/CD 143). This enzyme is a somatic form proteinase clearing peptide substrate, including core proteins of PGs.

Cell culture—Astrocytes cultures of human brain cells, derived from astrocytoma, U-87 MG (ATCC® HTB-14™, American Type Culture Collection, Rockville, Md., USA) were cultured in growth medium [10% Fetal Bovine Serum (FBS) and 1% Penicillin-Streptomycin solution (PS) in Minimum Essential Medium (MEM)]. Following, cells were harvested with trypsin-EDTA 0.25%, centrifuged, re-suspended for sub-culturing at 80% confluence, counted and re-suspended to a final concentration of $1\times10^6$/ml in assay medium (1% FBS). The cell suspension ($5\times10^5$ cells/well) was seeded into a 6-well plate (500 µl/well) containing 1.5 ml/well of assay medium, incubated for 24±1 hours at 37±10° C., 5% $CO_2$, and then examined microscopically. Following, at 90% cell confluence, the plates were treated according to the following groups:

untreated control;

2 activated controls [astrocytes activated with Bt2-cAMP (1 mM) alone or in combination with theophylline (0.25 mM)]; and 8 activated and treated with different anti-gliotic agents (i.e. astrocytes activated with Bt2-cAMP (1 mM) and theophylline (0.25 mM)+the indicated anti-gliotic agent).

The anti-gliotic agents were added as follows: Chondroitinase ABC (0.2 U/ml), Collagenase (2 mg, 50 µl), β-D-Xyloside (2.5 mM, 20 µl), MMPs-3 (0.5 µg, 20 µl), Anti TGFβ 1,2&3 (10 µg, 20 µl), Mitomycin C (50 µg, 25 µl), ACE human recombinant (0.5 µg, 25 µl) and Anti-Nogo A (5 U, 25 µl). 1 plate from each treatment was incubated for 48±1 hours at 37±10° C., 5% $CO_2$ followed by morphological evaluation and counting. In order to isolate and quantify $^{35}$S-GAG molecules from both the cells (intracellular and pericellular) and the medium, additional 3 plates from each treatment were added with 20 µCi radioactive $^{35}$S-radionucleotide [a carrier free sulfate that labels the accumulated biosynthesized GAG molecules by radioactivity ($^{35}$S-GAG), New England Nuclear via Perkin-Elmer Catalog number NEX041H specific activity 1050-1600 Ci/mM] and incubated for 48 hours. $^{35}$S-GAG isolation was effected as described by Weintstein et al. (Connect Tissue Res. 2012; 53(2):169-79).

Results

To examine the activity of anti-gliotic agents on activated astrocytes, in-vitro cultures of astrocytes were activated by both Bt2-cAMP and theophylline and treated with several anti-gliotic agents. The astrocytes activators, especially theophylline, significantly reduced the number of astrocytes in the culture, to 15.9%, while the Bt2-cAMP caused a milder reduction to 32.8% (Table 3). As shown in Table 3 below, most of the anti-gliotic agents added to the activated astrocytes cultures rescued the astrocytes from the activation induced cell death.

TABLE 3

In-vitro effect of anti-gliotic agents on astrocytes survival.

| Treatment | % of cells* |
|---|---|
| Untreated cells | 100.0 |
| Bt2-cAMP (activator) | 32.8 |
| Bt2-cAMP + Theophylline (activator) | 15.9 |
| Chondroitinase ABC | 33.1 |
| Collagenase | 39.1 |
| β-D-Xyloside | 54.7 |
| MMPs-3 | 23.2 |
| Anti TGFβ 1, 2&3 | 68.4 |
| Mitomycin C | 32.8 |
| ACE human recombinant | 70.4 |
| Anti-Nogo A | 80.5 |

*Cell percentage in astrocyte cultures relative to untreated cultures.

Astrocytes activation causes glycosaminoglycans (GAGs) accumulation in cultures, both intracellularly, pericellularly and extracellularly. Therefore, GAGs can serve as a tracer for either formation or elimination of the scar barrier.

As indicated above (Table 3), activation for 48 hours with Bt2-cAMP and theophylline, dramatically reduced the amount of cell survival to 32.8% and 15.9%, respectively. Therefore, in order to observe the actual effect of the anti-gliotic agents that were incubated with Bt2-cAMP and theophylline, the isolated $^{35}$S-GAGs were normalized according to the amount of vital cell survivors following 48 hours cultured with Bt2-cAMP and theophylline. Hence the 35S-GAGs isolated molecules amount for the theophylline well and all the treated wells were 6 times multiplied. The results summarized in Table 4 below, show that 5 of the 8 tested agents were able to reduce the levels of accumulated GAGs in the activated astrocytes cultures. The most efficient anti-gliotic agent in decreasing GAGs accumulation was chondroitinase ABC, which reduced the accomulation of $^{35}$S-GAGs to 5.5% relative to theophylline control; followed by Anti-Nogo A (15.3%), Anti TGFβ 1,2&3 (19.8%), mitomycin C (20.2%) and ACE human recombinant (22.9%).

TABLE 4

In-vitro effect of anti-gliotic agents on GAG accumulation.

| Treatment | Isolated $^{35}$S-GAGs Average + SD* | % of Isolated $^{35}$S-GAGs ** |
|---|---|---|
| Untreated cells | 12,173 + 1,700 | |
| Bt2-cAMP (activator) | 34,872 + 2,946 | |
| Bt2-cAMP + Theophylline (activator) | 77,717 + 13,778 | 100 |
| Chondroitinase ABC | 4,299 + 939 | 5.5 |
| β-D-xyloside | 61,016 + 21,506 | 78.5 |
| Collagenase Type I | 51,371 + 10,556 | 66.1 |
| Mitomycin C | 15,717 + 1,902 | 20.2 |
| MMPs-3 | 63,941 + 11,374 | 82.3 |
| Anti- Nogo A | 11,926 + 1,810 | 15.3 |
| Anti TGFβ 1, 2&3 | 15,390 + 6,213 | 19.8 |
| ACE human recombinant | 17,814 + 2,201 | 22.9 |

*The isolated $^{35}$S-GAGs of the cells were calculated relative to the amount of vital cell survivors in the Bt2-cAMP and theophylline control.
** GAGs percentage in astrocytes cultures relative to the theophylline control.

Example 2

In-Vitro Effects of AGRG on Neuronal Cells Survival

Materials and Methods

Chemicals—anti-gliotic agents as described in Example 1 above.

Guiding Regenerative Gel (GRG) and Anti-Gliotic Guiding Regenerative Gel (AGRG)—Hyaluronic acid-based hydrogel containing the anti-oxidant sodium dismutase and a laminin peptide (KSIKVAVRSYIGSRCV, SEQ ID NO: 1), denoted herein as guiding regenerative gel (GRG), was generated as disclosed in International Patent Application Publication No. WO2009/022339. Briefly, e.g. a 0.02% GRG was prepared from the three following components:

1. Hyaluronic Acid (HA): 1 Syringe of 2 ml gel of 1% Hyaluronic Acid (HA) in PBS (1:1 w/w) (Biotechnology-Ferring. Biotechnology General Israel Ltd. Israel) was added to a 50 ml tube.

2. Laminin peptide: Sixteen synthetic amino acids simulating laminin (SEQ ID NO: 1) containing the two cellular-biological active penta-peptides IKVAV-the epitope of laminin responsible for promoting neuronal outgrowth (SEQ ID NO: 2), and YIGSR the epitope of laminin responsible for promoting cell substrate adhesion (SEQ ID NO: 3) was obtained from LN, International Marketing Dept. of China-Peptide Co. Ltd., China. The laminin peptide was used in concentration of 50 µg solubilized in 1 ml of Phosphate buffered saline (PBS) and filtered through 0.45 micron filter paper. The filtered solution of 1 ml of LN peptide was added to the 50 ml tube containing the HA, all under sterile conditions.

3. Superoxide Dismutase (SOD): 20 µg SOD human recombinant (Merck Millipore Mercury, Israel) was solubilized in 1 ml of PBS.

Following, 1 ml of the sterilely filtered LM, 1 ml of sterile solution of SOD, 0.2 ml of hyaluronic acid and 2.8 ml PBS were mixed until receiving 5 ml of GRG in concentration of 0.02%. The GRG was kept at 2-4° C. forming homogenous transparent gel.

Anti-gliotic guiding regenerative gel (AGRG) is a hydrogel composed of a combination of GRG and anti-gliotic agents. Several AGRGs were generated by adding the respective anti-gliotic agent to a GRG and mixing. The AGRG was kept as 2-4° C. until use. To 5 ml GRG 0.02% the following anti-gliotic agents were added using a pipette: The Chondroitinase ABC (5 U/ml stock concentration) was diluted 1:50 (10 µl) in cell assay medium for AGRG1, AGRG4 and the last group. The mitomycin C (2 mg/ml stock concentration was diluted 1:80 (6.25 µl) in cell assay medium for AGRG2, AGRG4 and the last group. The Anti-human nogo (100 µg/ml stock concentration) was diluted 1:40 (12.5 µl) in cell assay medium for AGRG3, AGRG4 and the last group.

Cell culture—Neuronal cultures of human brain cells derived from metastatic site: bone marrow (neuroblastoma, SK-N-SH (ATCC® HTB-11™, American Type Culture Collection, Rockville, Md., USA) were cultured in growth medium [10% Fetal Bovine Serum (FBS) and 1% Penicillin-Streptomycin solution (PS) in Minimum Essential Medium (MEM)]. Following, cells were harvested at 80% confluence, counted and re-suspended to a final concentration in assay medium (1% FBS). The cell suspension (3×10$^5$ cells/well) was seeded in two 24-wells plates and incubated for 24±1 hours at 37±10° C., 5% CO$_2$ for 24 hours. Following incubation the cells were examined microscopically. In the next step various combinations of AGRGs were added to the cultures as follows:

Untreated cells,
GRG 0.02%,
Chondroitinase ABC+GRG 0.02% (denoted herein as AGRG1),
Mitomycin c+GRG 0.02% (denoted herein as AGRG2),
Anti-human nogo A+GRG 0.02% (denoted herein as AGRG3),
Chondroitinase ABC+mitomycin c+anti human nogo A+GRG 0.02% (denoted herein as AGRG4) and
Chondroitinase ABC+mitomycin c+anti-human nogo.

Triplicates were assayed from each treatment group.

Following incubation for 48±1 h at 37±1° C., 5% $CO_2$, cells from each treatment group were counted and the remaining replicates were photographed and processed for protein determination by the BCA Protein Assay (Thermo fisher Scientific, Catalog number 23225) according to manufacturer's instructions.

Results

To examine the activity of various AGRG combinations on neuronal cells in-vitro, neuronal cultures were treated with AGRG comprising GRG and one of Chondroitinase ABC, Anti-Nogo A or Mitomycin C, or GRG with Chondroitinase ABC, Anti-Nogo A and Mitomycin C; and compared to control cultures (un-treated cells, cells treated with GRG alone, or cells treated with the three anti-gliotic agents).

As shown in FIG. 1 and summarized in Table 5 below, addition of AGRG3 (GRG+Anti-Nogo A) increased significantly the number of neuronal cells in the culture, while treatment with GRG, combination of the three anti-gliotic agents and the other AGRG combinations decreased the number of cells. The results with AGRG2 and with the combination of the three anti-gliotic agents indicated that the anti-gliotic agent Mitomycin C is highly toxic to neuronal cells, although it had a strong anti-gliotic influence on activated astrocytes (as shown in Example 1 above).

TABLE 5

In-vitro effect of AGRG on neuronal cells survival.

| Treatment | % of cells* |
|---|---|
| Untreated cells | 100 |
| GRG 0.02% | 98 |
| AGRG1: GRG 0.02% + Chondroitinase ABC | 61 |
| AGRG2: GRG 0.02% + Mitomycin C | 2 |
| AGRG3: GRG 0.02% + Anti-Nogo A | 133 |
| AGRG4: GRG 0.02% + Chondroitinase ABC + Mitomycin C + Anti-Nogo A | 14 |
| Chondroitinase ABC + Mitomycin C + Anti-Nogo A | 4 |

*Cell percentage in neuronal cultures relative to un-treated cells cultures.

Protein content can indicate cells condition, as typically high protein content indicates a better condition. Hence, to further examine cell quality, protein concentration analysis of the above cultures was performed. As shown in Table 6 below, protein content following AGRG3 treatment was 88.07% as compared to the untreated control, while protein content following AGRG2 treatment was very poor. Surprisingly, protein content following AGRG1 treatment was the highest (97.14%) compared to all other treatment, while the number of cells was reduced to 61% (Table 6 above); indicating Chondroitinase ABC as an additional anti-gliotic candidate for the AGRG.

Taken together, out of the three most efficient anti-gliotic agents found on the astrocytes culture assay (Example 1, Chondroitinase ABC, Anti-Nogo A and Mitomycin C), anti-Nogo A is the most promising anti-gliotic agent to be combined with GRG.

TABLE 6

In-vitro effect of AGRG on protein content in neuronal cells

| Treatment | % of protein* |
|---|---|
| Untreated cells | 100.00 |
| GRG 0.02% | 91.62 |
| AGRG1: GRG 0.02% + Chondroitinase ABC | 97.14 |
| AGRG2: GRG 0.02% + Mitomycin C | 53.69 |
| AGRG3: GRG 0.02% + Anti-Nogo A | 88.07 |
| AGRG4: GRG 0.02% + Chondroitinase ABC + Mitomycin C + Anti-Nogo A | 59.24 |
| Controls: Chondroitinase ABC + Mitomycin C + Anti-Nogo A | 42.46 |

*Protein percentage in neuronal cultures relative to un-treated cells cultures.

Example 3

In-Vitro Effects of AGRG on Astrocytes and Neuronal Cells Co-Culture Survival Compared to GRG or Anti-Gliotic Agents Chemicals—anti-gliotic agents as described in Example 1 above.

GRG and AGRG—as described in Example 2 above. Various concentrations between 0.02% and 0.6% of GRG are prepared.

Astrocytes Cell culture—As described in Example 1 above.

Treatment groups include:

| Wells | | Treatment |
|---|---|---|
| 1-4 | Untreated | none |
| 5-8 | astrocytes | GRG |
| 9-12 | | Anti nogo A |
| 13-16 | | Chondroitinase ABC |
| 17-20 | | AGRG comprising GRG + Anti nogo A |
| 21-24 | | AGRG comprising GRG + Chondroitinase ABC |
| 25-28 | | Anti nogo A + Chondroitinase ABC |
| 29-32 | | AGRG comprising GRG + Anti nogo A + Chondroitinase ABC |
| 33-36 | Active | Bt2-cAMP + Theophylline |
| 37-40 | astrocytes | Bt2-cAMP + Theophylline + GRG |
| 41-44 | | Bt2-cAMP + Theophylline + Anti nogo A |
| 45-48 | | Bt2-cAMP + Theophylline + Chondroitinase ABC |
| 49-52 | | Bt2-cAMP + Theophylline + AGRG comprising GRG + Anti nogo A |
| 53-56 | | Bt2-cAMP + Theophylline + AGRG comprising GRG + Chondroitinase ABC |
| 57-60 | | Bt2-cAMP + Theophylline + Anti nogo A + Chondroitinase ABC |
| 61-64 | | Bt2-cAMP + Theophylline + AGRG comprising GRG + Anti nogo A + Chondroitinase ABC |

Neuronal Cell culture—As described in Example 2 above.
Treatment groups include:
Untreated cells,
GRG,
Anti nogo A,
Chondroitinase ABC,
AGRG comprising GRG+Anti nogo A,
AGRG comprising GRG+Chondroitinase ABC,
Anti nogo A+Chondroitinase ABC,
AGRG comprising GRG+Anti nogo A+Chondroitinase ABC.

Combined astrocytes and neuronal cells culture—Cell cultures of human brain cell derived from astrocytoma and human brain cells derived from metastatic site: bone marrow (U-87 MG, ATCC® HTB-14™ and neuroblastoma, SK-N-SH, ATCC® HTB-11™, American Type Culture Collection, Rockville, Md., USA, respectively) are cultured in growth medium (10% Fetal Bovine Serum (FBS) and 1% Penicillin-Streptomycin solution (PS) in Minimum Essential Medium (MEM)). Following, the cells are harvested with trypsin-EDTA 0.25%, centrifuged and re-suspended for sub-culturing. The cells are counted at 80% confluence and re-suspended to a final concentration $1 \times 10^6$/ml in assay medium (1% FBS). The cell suspension ($5 \times 10^5$ cells/well) is seeded into the 6-well plate (500 μl/well) containing 1.5 ml/well of assay medium and incubated for 24±1 hours at 37±10° C., 5% $CO_2$. Following incubation the cells are examined microscopically. At 90% cell confluence, the plates are treated according to the following groups:

| Wells | | Treatment |
|---|---|---|
| 1-4 | Untreated | none |
| 5-8 | astrocytes | GRG |
| 9-12 | | Anti nogo A |
| 13-16 | | Chondroitinase ABC |
| 17-20 | | AGRG comprising GRG + Anti nogo A |
| 21-24 | | AGRG comprising GRG + Chondroitinase ABC |
| 25-28 | | Anti nogo A + Chondroitinase ABC |
| 29-32 | | AGRG comprising GRG + Anti nogo A + Chondroitinase ABC |
| 33-36 | Active | Bt2-cAMP + Theophylline |
| 37-40 | astrocytes | Bt2-cAMP + Theophylline + GRG |
| 41-44 | | Bt2-cAMP + Theophylline + Anti nogo A |
| 45-48 | | Bt2-cAMP + Theophylline + Chondroitinase ABC |
| 49-52 | | Bt2-cAMP + Theophylline + AGRG comprising GRG + Anti nogo A |
| 53-56 | | Bt2-cAMP + Theophylline + AGRG comprising GRG + Chondroitinase ABC |
| 57-60 | | Bt2-cAMP + Theophylline + Anti nogo A + Chondroitinase ABC |
| 61-64 | | Bt2-cAMP + Theophylline + AGRG comprising GRG + Anti nogo A + Chondroitinase ABC |

The following concentrations are used: Bt2-cAMP—1 mM, Theophylline—0.25 mM, GRG—various concentration between 0.02% and 0.5%, Anti nogo A—200 μg/ml stock concentration diluted 1:40 (12.5 μl) in cell assay medium and Chondroitinase ABC—5 U/ml stock concentration diluted 1:50 (10 μl) in cell assay medium. One plate from each treatment is incubated for 48 hours at 37±10° C., 5% CO2; and following incubation evaluated morphologically and counted. Additional 3 plates from each treatment are added with a 20 μCi radioactive $^{35}$S-radionucleotide and treated as described in Example 1 above.

Example 4

In-Vivo Effects of AGRG on Neuronal Regeneration

Materials and Methods

Chemicals—anti-gliotic agents as described in Example 1 above.

GRG and AGRG—as described in Example 2 above, with the following modifications: GRG concentration 0.4% (1 ml of the sterilely filtered LM, 1 ml of sterile solution of SOD, 2 ml of hyaluronic acid and 1 ml PBS were mixed until receiving 5 ml of GRG in concentration of 0.4%) 5 μl of anti nogo A (200 U, Enco Scientific services LTD., Israel), 4 μl of Chondroitinase ABC (5 U, Sigma Aldrich Israel LTD., Israel).

Acute complete spinal cord injury (SCI) model—Twenty Sprague-Dawley rats weighing approximately 250 gr each were operated and followed for up to 6 months. All surgical procedures were performed using a high magnification microscope. The spinal cord was exposed via a dorsal approach. The overlying muscles were retracted and the T7-T8 laminae removed, the spinal cord was completely transected using micro-scissors and a 2 mm segment of the cord was removed. Each animal was earmarked and randomly allocated to the various treatment groups, according to a randomization list generated before the initiation of the study:

1. Control group—rats with complete SCI with no further treatment.
2. Implantation of GRG in the transected area of the spinal cord, in direct contact with the margins of the two stumps.
3. Implantation of AGRG (GRG and anti nogo A) in the transected area of the spinal cord, in direct contact with the margins of the two stumps.

The entire area of the lesion was covered with a thin biodegradable membrane (Lyodura, AESCULAP), composed of the biological co-polymer, attached by surgical adhesive (BioGlue, CryoLife) for fixation of the implants at the desired sites. Finally, the muscular and cutaneous planes were closed and sutured.

Post-operative animal care was performed to minimize discomfort and pain. The first two weeks after surgery are considered the most critical for the rats to survive; thus, analgesia was given during the first 5 days following the surgery, which includes antibiotics and pain medication. In addition, the rats were assisted in urination and defecation with the help of a veterinarian, twice a day. Animals were maintained in ventilated cages, containing sterile sawdust and sterile food. The paraplegic rats were kept solitary in cages, but were gathered in groups for 1 hour every day, in a large facility. The rats were monitored up to 6 months, while several rats from each group were monitored for 1 or 3 months. At the termination of the experiments, the animals (n=3 for each group) were sacrificed under general anesthesia.

Electrophysiological measurements—Somatosensory evoked potentials (SSEP) was recorded in each rat immediately postoperatively and later on once a month. Conductivity of the spinal cord was studied by stimulation of the sciatic nerve and recording from two disc-recording electrodes, active and reference, placed on the rats' scalps. These electrodes were attached to the scalp—an active electrode over the somatosensory cortex in the midline and a reference electrode between the two eyes. The earth electrode was placed on the thigh, on the side of the stimulation. The sciatic nerve was stimulated by a bipolar stimulating electrode. Two hundred and fifty-six stimulation pulses of 0.1 ms in duration were generated at a rate of 3 $s^{-1}$. The stimulus intensity was increased gradually, until detection of slight twitching of the limb. The appearance of evoked potentials, as a response to stimulation in two consecutive tests, was considered positive.

Functional tests—Evaluated by testing locomotor activity of individual animals according to the 21-point open-field Basso-Beattie-Bresnahan (BBB) scale. A score of 0 was given for no spontaneous hind limb movement, while a score of 21 indicated a normal locomotion. This test was carried out every 7 days after the surgery.

Histology—Rats were sacrificed and spinal cord segments were collected from all tested rats. The samples were taken both proximally and distally to the injury site and fixed in 4% paraformaldehyde solution. Three cross sections were made from each spinal cord sample: proximal part, lesion area and distal part. The tissues were trimmed, embedded in paraffin, sectioned at approximately 2-3 microns thickness and stained with either Choline Acetyltransferase (CHAT, staining of motor neurons) or Neuro Filament (NF, staining of all nerves fibers). The samples were evaluated using a fluorescence microscope, counting both the number of nerve fibers and the sizes of the fibers (under 4 μm or over it).

Results

The in-vivo effect of AGRG on nerve regeneration was evaluated in a complete spinal cord injury (SCI) rat model using an AGRG composed of GRG and anti-nogo A. The results clearly showed that the AGRG implantation at or near the site of SCI promoted nerve regeneration in this model; and specifically:

1. Improved movement in previously paralyzed limbs—Basso-Beattie-Bresnahan scale (BBB) score of the AGRG group reached 6, 60 days post SCI; namely the rat was able to move extensively at least one or two joints and slight of the third joint, while in the untreated control group the score reached between 0 to 1 and in rat treated with GRG the score reached 3 with only a slight movement detected (FIGS. 2A-C).

2. Promoted regaining of conductivity in the previously paralyzed limbs—regained conductivity (somatosensory evoked potentials) was evident in the AGRG group beginning 60 days post SCI, while no conductivity was found in the untreated control group (FIG. 3).

3. Promoted axonal penetration through the glial scar barrier—Neurofilament (NF) staining, which stains all neuronal fibers, revealed neuronal fibers in all cross sections of the injured spinal cord implanted with AGRG: proximal position, lesion area and distal position (FIG. 4), namely, AGRG was able to promote axonal sprouting through the glial scar. In comparison, NF staining of spinal cord from an untreated control rat exhibited neuronal fibers only at the proximal and distal positions with no sprouting at the lesion area.

Taken together, the AGRG comprising GRG and anti-nogo A provided an optimal environment for neuronal regeneration by enhancing axonal growth and sprouting, on the one hand, and by reducing the scar barrier and preventing its further formation, on the other.

Example 5

In Vivo Effects of AGRG on Neuronal Regeneration Compared to GRG or Anti-Gliotic Agents Chemicals—anti-gliotic agents as described in Example 1 above.

GRG and AGRG—as described in Example 2 above. Various concentrations between 0.02% and 0.6% of GRG are prepared.

Acute complete spinal cord injury (SCI) model—as described in Example 4 above.

Treatment groups include:
1. Control group—rats with complete SCI with no further treatment.
2. Implantation of GRG in the transected area of the spinal cord, in direct contact with the margins of the two stumps.
3. Implantation of AGRG (GRG and anti nogo A) in the transected area of the spinal cord, in direct contact with the margins of the two stumps.
4. Implantation of AGRG (GRG and Chondroitinase ABC) in the transected area of the spinal cord, in direct contact with the margins of the two stumps.
5. Implantation of AGRG (GRG and Chondroitinase ABC and anti nogo A) in the transected area of the spinal cord, in direct contact with the margins of the two stumps.
6. Implantation of anti-nogo A in the transected area of the spinal cord.
7. Implantation of Chondroitinase ABC in the transected area of the spinal cord.
8. Implantation of anti-nogo A+Chondroitinase ABC in the transected area of the spinal cord.

Electrophysiological measurements, Functional tests and Histology—as described in Example 4 above.

Example 6

In-Vivo Effects of AGRG on Prevention of Neurogenic Shock and Mortality Following Spinal Cord Injury Materials and Methods Chemicals—anti-gliotic agents as described in Example 1 above.

AGRG—as described in Example 2 above. A concentration of 0.4% of GRG was prepared.

Acute complete spinal cord injury (SCI) model—as described in Example 4 above.

Treatment groups include:
1. Control group—rats with complete SCI with no further treatment.
2. Implantation of AGRG (GRG and anti nogo A) in the transected area of the spinal cord, in direct contact with the margins of the two stumps.
3. Implantation of AGRG (GRG and Chondroitinase ABC) in the transected area of the spinal cord, in direct contact with the margins of the two stumps.

Statistical analysis—Chi-squared test was used to evaluate the statistical significance of survival rate between the treatment groups.

Results

To evaluate the effect of AGRG on neurogenic shock and morbidity following SCI, the survival rate of rats has been evaluated (rats sacrificed for histology evaluation, during the first 7 weeks post-surgery, weren't taken into account). As shown in FIG. 5, AGRG had a protective effect against spinal shock: about half of the control rats died from spinal shock (due to the surgical SCI procedure) during the first 72 hours, while about 80% of the rats treated with either of the AGRGs survived. Taken together, the AGRG comprising GRG and anti-nogo A or Chondroitinase ABC decreased the mortality rate in the SCI treated rats.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES (Additional References are Cited in Text)

1. Asher R A, Morgenstern D A, Moon L D, Fawcett J W. Chondroitin sulphate proteoglycans: inhibitory components of the glial scar. Prog Brain Res. 2001; 132:611-9.

2. Asher R A, Morgenstern D A, Properzi F, Nishiyama A, Levine J M, Fawcett J W. Two separate metalloproteinase activities are responsible for the shedding and processing of the NG2 proteoglycan in vitro. Mol Cell Neurosci. 2005 May; 29(1):82-96.

4. Barritt A W, Davies M, Marchand F, Hartley R, Grist J, Yip P, McMahon S B, Bradbury E J. Chondroitinase ABC promotes sprouting of intact and injured spinal systems after spinal cord injury. J Neurosci. 2006 Oct. 18; 26(42):10856-67.

5. Bosch K D, Bradbury E J, Verhaagen J, Fawcett J W, McMahon S B. Chondroitinase ABC promotes plasticity of spinal reflexes following peripheral nerve injury. Exp Neurol. 2012 November; 238(1):64-78.

6. Bovolenta P, Fernaud-Espinosa I. Nervous system proteoglycans as modulators of neurite outgrowth. Prog Neurobiol. 2000 June; 61(2):113-32.

7. Bradbury E J, Moon L D, Popat R J, King V R, Bennett G S, Patel P N, Fawcett J W, McMahon S B. Chondroitinase ABC promotes functional recovery after spinal cord injury. Nature. 2002 Apr. 11; 416(6881):636-40.

8. Brittis P A, Flanagan J G. Nogo domains and a Nogo receptor: implications for axon regeneration. Neuron. 2001 April; 30(1):11-4. Review. No abstract available.

9. Bruce J H, Norenberg M D, Kraydieh S, Puckett W, Marcillo A, Dietrich D. Schwannosis: role of gliosis and proteoglycan in human spinal cord injury. J Neurotrauma. 2000 September; 17(9):781-8.

3. Canning D R, Höke A, Malemud C J, Silver J. A potent inhibitor of neurite outgrowth that predominates in the extracellular matrix of reactive astrocytes. Int J Dev Neurosci. 1996 June; 14(3):153-75.

4. Challacombe J F, Elam J S. Inhibition of proteoglycan synthesis influences regeneration of goldfish retinal axons on polylysine and laminin. Exp Neurol. 1995 July; 134(1):126-34.

5. Chau C H, Shum D K, Li H, Pei J, Lui Y Y, Wirthlin L, Chan Y S, Xu X M. Chondroitinase ABC enhances axonal regrowth through Schwann cell-seeded guidance channels after spinal cord injury. FASEB J. 2004 January; 18(1):194-6. Epub 2003 Nov. 20.

6. Chen M S1, Huber A B, van der Haar M E, Frank M, Schnell L, Spillmann A A, Christ F, Schwab M E. Nogo-A is a myelin-associated neurite outgrowth inhibitor and an antigen for monoclonal antibody IN-1. Nature. 2000 Jan. 27; 403(6768):434-9.

7. Faulkner J R, Herrmann J E, Woo M J, Tansey K E, Doan N B, Sofroniew M V. Reactive astrocytes protect tissue and preserve function after spinal cord injury. J Neurosci. 2004 Mar. 3; 24(9):2143-55.

8. Fawcett J W, Asher R A. The glial scar and central nervous system repair. Brain Res Bull. 1999 August; 49(6):377-91. Review.

9. Fitch M T, Silver J. Glial cell extracellular matrix: boundaries for axon growth in development and regeneration. Cell Tissue Res. 1997 November; 290(2):379-84. Review.

10. Fitch M T, Silver J. CNS injury, glial scars, and inflammation: Inhibitory extracellular matrices and regeneration failure. Exp Neurol. 2008 February; 209(2):294-301. Epub 2007 May 31. Review.

11. Goldberg J L, Barres B A. Nogo in nerve regeneration. Nature. 2000 Jan. 27; 403(6768):369-70. No abstract available.

12. Grandpré T, Strittmatter S M. Nogo: a molecular determinant of axonal growth and regeneration. Neuroscientist. 2001 October; 7(5):377-86. Review.

13. Hermanns S, Klapka N, Muller H W. The collagenous lesion scar—an obstacle for axonal regeneration in brain and spinal cord injury. Restor Neurol Neurosci. 2001; 19(1-2):139-48. Review.

14. Jones L L, Yamaguchi Y, Stallcup W B, Tuszynski M H. NG2 is a major chondroitin sulfate proteoglycan produced after spinal cord injury and is expressed by macrophages and oligodendrocyte progenitors. J Neurosci. 2002 Apr. 1; 22(7):2792-803.

15. Laabs T L1, Wang H, Katagiri Y, McCann T, Fawcett J W, Geller H M. Inhibiting glycosaminoglycan chain polymerization decreases the inhibitory activity of astrocyte-derived chondroitin sulfate proteoglycans. J Neurosci. 2007 Dec. 26; 27(52):14494-501.

16. Lang B T, Cregg J M, DePaul M A, Tran A P, Xu K, Dyck S M, Madalena K M, Brown B P, Weng Y L, Li S, Karimi-Abdolrezaee S, Busch S A, Shen Y, Silver J. Modulation of the proteoglycan receptor PTPσ promotes recovery after spinal cord injury. Nature. 2015 Feb. 19; 518(7539):404-8.

17. Lemons M L, Howland D R, Anderson D K. Chondroitin sulfate proteoglycan immunoreactivity increases following spinal cord injury and transplantation. xp Neurol. 1999 November; 160(1):51-65.

18. Lu P, Jones L L, Tuszynski M H. Axon regeneration through scars and into sites of chronic spinal cord injury. Exp Neurol. 2007 January; 203(1):8-21. Epub 2006 Oct. 2.

19. McKeon R J1, Schreiber R C, Rudge J S, Silver J. Reduction of neurite outgrowth in a model of glial scarring following CNS injury is correlated with the expression of inhibitory molecules on reactive astrocytes. J Neurosci. 1991 November; 11(11):3398-411.

20. McKeon R J, Höke A, Silver J. Injury-induced proteoglycans inhibit the potential for laminin-mediated axon growth on astrocytic scars. Exp Neurol. 1995 November; 136(1):32-43.

21. Minor K, Jasper, K, Fulgham S, Davies J. R., Davies S. J. A. Intrathecal Infusion of Decorin to Subacute and Long-Term Chronic Contusion Spinal Cord Injuries promotes robust functional recovery. Neurosurgery 71(2):E576; 2012.

22. Morgenstern D A, Asher R A, Fawcett J W. Chondroitin sulphate proteoglycans in the CNS injury response. Prog Brain Res. 2002; 137:313-32. Review.

23. Norenberg M D. Astrocyte responses to CNS injury. J Neuropathol Exp Neurol. 1994 May; 53(3):213-20.

24. Ohtake Y, Li S. Molecular mechanisms of scar-sourced axon growth inhibitors. Brain Res. 2015 Sep. 4; 1619:22-35.

25. Shimon Rochkind, Zvi Nevo Polypeptides, matrices, hydrogels and methods of using same for tissue regeneration and repair Publication number U.S. Pat. No. 8,242,076 B2 Publication date Aug. 14, 2012

26. Rudge J S, Silver J. Inhibition of neurite outgrowth on astroglial scars in vitro. J Neurosci. 1990 November; 10(11): 3594-603.

27. Siebert J R, Conta Steencken A, Osterhout D J. Chondroitin sulfate proteoglycans in the nervous system: inhibitors to repair. Boomed Res Int. 2014; 2014:845323.

28. Silver J. Inhibitory molecules in development and regeneration. J Neurol. 1994 242(1 Suppl 1):522-4. Review.

29. Silver J, Miller J H. Regeneration beyond the glial scar. Nat Rev Neurosci. 2004 February; 5(2):146-56. Review. No abstract available.

30. Smith-Thomas L C, Stevens J, Fok-Seang J, Faissner A, Rogers J H, Fawcett J W.

31. Increased axon regeneration in astrocytes grown in the presence of proteoglycan synthesis inhibitors. J Cell Sci. 1995 March; 108 (Pt 3):1307-15.

32. Sofroniew M V, Vinters H V. Astrocytes: biology and pathology. Acta Neuropathol. 2010 January; 119(1):7-35.

33. Weinstein T, Evron Z, Trebicz-Geffen M, Aviv M, Robinson D, Kollander Y, Nevo Z. β-D-xylosides stimulate GAG synthesis in chondrocyte cultures due to elevation of the extracellular GAG domains, accompanied by the depletion of the intra-pericellular GAG pools, with alterations in the GAG profiles. Connect Tissue Res. 2012; 53(2):169-79.

34. Yick L W, Wu W, So K F, Yip H K, Shum D K. Chondroitinase ABC promotes axonal regeneration of Clarke's neurons after spinal cord injury. Neuroreport. 2000 Apr. 7; 11(5):1063-7.

35. Young W. Spinal cord regeneration. Cell Transplant. 2014; 23(4-5):573-611. doi: 10.3727/096368914X678427. Review.

36. Xu B, Park D, Ohtake Y, Li H, Hayat U, Liu J, Selzer M E, Longo F M, Li S. Role of CSPG receptor LAR phosphatase in restricting axon regeneration after CNS injury. Neurobiol Dis. 2015 January; 73:36-48.

37. Zuo J1, Neubauer D, Graham J, Krekoski C A, Ferguson T A, Muir D. Regeneration of axons after nerve transection repair is enhanced by degradation of chondroitin sulfate proteoglycan. Exp Neurol. 2002 July; 176(1):221-8.

38. Piepmeyer J M, Lehmann K B and Lane J G. Cardiovascular instability following acute cervical spine trauma. Cent Nerv Syst Trauma, 1985; 2(3):153-160.

39. Guly H R and Lecky F E. The incidence of neurogenic shock in patients with isolated Spinal cord injury in the emergency department. Resuscitation, 2008; 76(1): 57-62.

What is claimed is:

1. A composition comprising a hyaluronic acid, a laminin polypeptide, an antioxidant and Copaxone.

2. The composition of claim 1, wherein said antioxidant is superoxide dismutase (SOD).

3. The composition of claim 2, wherein said SOD comprises the amino acid sequence set forth by SEQ ID NO: 4.

4. The composition of claim 1, wherein said laminin polypeptide is set forth by SEQ ID NO: 1.

5. The composition of claim 1, wherein said antioxidant is superoxide dismutase (SOD) comprising the amino acid sequence set forth by SEQ ID NO: 4 and said laminin polypeptide is set forth by SEQ ID NO: 1.

6. The composition of claim 1, wherein said hyaluronic acid, said antioxidant and said laminin polypeptide are cross linked.

7. A matrix comprising the composition of claim 1.

8. A hydrogel comprising the composition of claim 1.

9. The hydrogel of claim 8, wherein said hyaluronic acid is provided at a concentration range of about 0.5-1.5% in said hydrogel; and/or wherein said laminin polypeptide is provided at a concentration range of about 20-100 µg/ml in said hydrogel; and/or wherein said antioxidant is provided at a concentration range of about 5-40 µg/ml in said hydrogel; and/or wherein said hyaluronic acid, said laminin polypeptide and said antioxidant are provided at a total concentration of about 0.01 0.6%; and/or wherein said hyaluronic acid, said laminin polypeptide and said antioxidant are provided at a total concentration of about 0.4%; and/or wherein said Copaxone is provided at a concentration range of about 5-300 µg/ml in said hydrogel.

10. The composition of claim 1, wherein said antioxidant is selected from the group consisting of glutathione, vitamin C, vitamin E, N-Ac-L-cysteine, hydroquinone, glutamate, catalase, peroxidase, superoxide dismutase, glutathione peroxidase and glucose-6-phosphate dehydrogenase (G6PD).

11. The composition of claim 1, wherein said antioxidant is vitamin E.

12. A method of inducing formation or regeneration of a neuronal tissue in a subject in need thereof, the method comprising implanting the composition of claim 1 in the subject, thereby inducing the formation or regeneration of the neuronal tissue in the subject.

13. A method of treating nerve injury in a subject in need thereof, the method comprising implanting the composition of claim 1 at or near the nerve injury of the subject, thereby treating the nerve injury in the subject.

14. The method of claim 13, wherein said nerve injury is part of the central nervous system (CNS).

15. The method of claim 13, wherein said nerve injury comprises spinal cord injury (SCI).

16. The method of claim 13, wherein said nerve injury comprises traumatic brain injuries (TBI) or traumatic optic neuropathy (TON).

17. A method of preventing or treating neurogenic shock following nerve injury in a subject in need thereof, the method comprising implanting the composition of claim 1 at or near the nerve injury of the subject, thereby preventing or treating the neurogenic shock in the subject.

18. The method of claim 17, wherein said implanting is effected within 48 hours following said nerve injury.

19. A method of generating a hydrogel, the method comprising:
   (i) suspending a composition comprising a hyaluronic acid, a laminin polypeptide and an antioxidant in water so as to obtain a suspension which comprises at least 40% water; and
   (ii) adding Copaxone to said suspension, thereby generating the hydrogel.

* * * * *